(12) United States Patent
Alexander et al.

(10) Patent No.: US 12,385,922 B2
(45) Date of Patent: Aug. 12, 2025

(54) SIZE-BASED GATING TO ANALYZE FLOW CYTOMETRY DATA

(71) Applicant: Ventana Medical Systems, Inc., Tucson, AZ (US)

(72) Inventors: Nelson R. Alexander, Marana, AZ (US); Aoune Barhoumi, Oro Valley, AZ (US); Lisa L. Gallegos, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 541 days.

(21) Appl. No.: 17/203,832

(22) Filed: Mar. 17, 2021

(65) Prior Publication Data

US 2021/0270837 A1 Sep. 2, 2021

Related U.S. Application Data

(63) Continuation of application No. PCT/EP2019/074952, filed on Sep. 18, 2019.

(60) Provisional application No. 62/733,829, filed on Sep. 20, 2018.

(51) Int. Cl.
| | |
|---|---|
| *G01N 33/574* | (2006.01) |
| *G01N 15/14* | (2006.01) |
| *G01N 15/1429* | (2024.01) |
| *G01N 15/10* | (2006.01) |

(52) U.S. Cl.
CPC ... *G01N 33/57484* (2013.01); *G01N 15/1429* (2013.01); *G01N 15/1459* (2013.01); *G01N 2015/1006* (2013.01); *G01N 2015/1402* (2013.01)

(58) Field of Classification Search
CPC .............................................. G01N 33/57484
USPC ....................................................... 435/7.23
See application file for complete search history.

(56) References Cited

U.S. PATENT DOCUMENTS

| | | | |
|---|---|---|---|
| 6,767,737 B1* | 7/2004 | Wilson | C12N 5/0665 435/372 |
| 9,910,039 B2 | 3/2018 | Garcia Santana | |
| 10,782,298 B2 | 9/2020 | Patterson et al. | |
| 11,959,838 B2 | 4/2024 | Alexander et al. | |
| 2014/0349313 A1 | 11/2014 | Balderas et al. | |
| 2015/0337384 A1 | 11/2015 | Bartunkova et al. | |
| 2016/0123980 A1 | 5/2016 | Evans et al. | |
| 2018/0136214 A1 | 5/2018 | Patterson et al. | |
| 2018/0252708 A1 | 9/2018 | De | |
| 2018/0356420 A1 | 12/2018 | Volovitz et al. | |
| 2020/0049599 A1 | 2/2020 | Alexander et al. | |
| 2023/0065632 A1 | 3/2023 | Volovitz et al. | |

FOREIGN PATENT DOCUMENTS

| | | |
|---|---|---|
| CN | 103782173 A | 5/2014 |
| CN | 105378066 A | 3/2016 |
| CN | 108449995 A | 8/2018 |
| JP | 2015526709 A | 9/2015 |
| JP | WO2018016656 A1 | 9/2019 |
| WO | 2017079763 A1 | 5/2017 |
| WO | 2017094008 A1 | 6/2017 |
| WO | 2018016656 A1 | 1/2018 |
| WO | 2018048936 A1 | 3/2018 |

OTHER PUBLICATIONS

Cano et al (Autoimmunity: From Bench to Bedside, Chapter 5 Introduction to T and B lymphocytes, El Rosario University Press, Jul. 18, 2013).*
Rathore et al (Indian J Med Res, 2014, 140: 361-369).*
Daniil et al (Respiratory Research, 2005, 6(81): 1-8).*
Grange et al (Journal of Immunological Methods, 2011, 372: 119-126).*
Givan (Flow Cytometry Protocols, Third Edition, Humana Press, 2011, Chapter 1, "Flow Cytometry: An Introduction", pp. 1-29).*
Turksma et al (Clinical Cancer Research, 2016, 22(2): 346-356).*
Hristov et al (Cytometry Part A, 2009, 775A: 848-853).*
Hao et al (Advanced Drug Delivery, 2018, 125: 3-20).*
Strokotov et al (Journal of Biomedical Optics, 2009, 14(6): 1-12).*
International Search Report and Written Opinion, dated Feb. 1, 2020.
Karolina Woroniecka et al, "Flow Cytometric Identification of Tumor-Infiltrating Lymphocytes from Glioblastoma : Methods and Protocols", "Methods in Molecular Biology", p. 221-226, Jan. 1, 2018 (Jan. 1, 2018), US Humana Press, New York, NY.
Magdalena Kovacsovics-Bankowski et al, "Detailed characterization of tumor infiltrating lymphocytes in two distinct human solid malignancies show phenotypic similarities", Journal for Immunotherapy of Cancer, 33rd Annual Meeting & Pre-Conference Programs of the Society for Immunotherapy of Cancer (SITC 2018), vol. 2, No. 1, Nov. 18, 2014 (Nov. 18, 2014), p. 1-12.
A. Richter et al, "Tumor infiltrating T cells: complete workflows allow faster and improved flow cytometric analysis of syngeneic mouse tumors," Jul. 2, 2018 (Jul. 2, 2018), DOI: 10.1158-7445,AM2018-LB-351.
Santegoets Saskia J et al, "Monitoring regulatory T cells in clinical samples: consensus on an essential marker set and gating strategy for regulatory T cell analysis by flow cytometry", Jun. 28, 2015 (Jun. 28, 2015), vol. 64, No. 10, p. 1271-1286, DOI: 10.1007/S00262-015-1729-X.

* cited by examiner

*Primary Examiner* — Sean E Aeder
(74) *Attorney, Agent, or Firm* — Charney IP Law LLC; Thomas M. Finetti

(57) ABSTRACT

Disclosed herein is a method of analyzing flow cytometry data for cells derived from homogenized whole tumor samples.

8 Claims, 18 Drawing Sheets

SIZE-BASED GATING TO ANALYZE FLOW CYTOMETRY DATA

CROSS REFERENCE TO RELATED APPLICATIONS

This application is a continuation of International Application No. PCT/EP2019/074952 filed on Sep. 18, 2019, which application claims the benefit of the filing date of U.S. Patent Application No. 62/733,829, which application was filed on Sep. 20, 2018, the disclosures of which are hereby incorporated by reference herein in their entireties.

BACKGROUND OF THE DISCLOSURE

Cancer is a disease marked by the uncontrolled proliferation of abnormal cells. In normal tissue, cells divide and organize within the tissue in response to signals from surrounding cells, resulting in normal cellular behavior that is carefully orchestrated by the tissue context. Cancer cells do not respond to growth-limiting contextual cues from the surrounding tissue, and they often harbor genetic alterations that drive them to proliferate and, in many organs, form a tumor. As the growth of a tumor progresses, genetic and phenotypic alterations continue to accumulate, allowing populations of cancer cells to overcome additional "checkpoints," such as an anti-tumor immune response, and manifesting as a more aggressive growth phenotype of the cancer cells. If left untreated, metastasis, the spread of cancer cells to distant areas of the body by way of the lymphatic system or bloodstream, may ensue. Metastasis results in the formation of secondary tumors at multiple sites, damaging healthy tissue. Most cancer death is caused by such secondary tumors.

Despite decades of advances in cancer diagnosis and therapy, many cancers continue to go undetected until late in their development. As a result, many solid tumors at the initial site of growth contain genetically and/or phenotypically heterogeneous tumor cell populations that are often spatially segregated. One or more of these cancer cell populations within the primary tumor may give rise to the secondary metastatic tumors. In addition, the tumor mass often consists of normal cells that are either recruited by the tumor to form a supportive environment (e.g. blood vessels) or were initially drawn to the tumor as a defensive mechanism by the host (e.g. immune cells) but were later overcome as the cancer evolved.

One technique for accounting, examining, and sorting multiple analytes, including cell populations, occurring in a biological sample, such as a sample derived from a tumor sample or tumor mass, involves flow cytometry. Flow cytometry allows simultaneous multiparametric analysis of physical and/or chemical characteristics of particles flowing through optical and/or electronic detection apparatuses. Current optical detection systems monitor changes in light scatter and fluorescence. Electronic detection is achieved by suspending particles in conducting fluid, then passing them through a small aperture or orifice. An electronic field is applied across the aperture or orifice, creating a current. When a particle passes through the aperture, the resistance across the orifice increases. The increase in resistance at constant current results in an increase in voltage across the orifice, which is directly related to the volume of the particle. The measurable voltage pulse is generated which can be analyzed and used to conduct further operations such as conductivity, resistivity, capacitance and shape modeling of the particle.

BRIEF SUMMARY OF THE DISCLOSURE

Applicant has developed a new approach of sampling tumors such that meaningful information may be derived from the sampled tumor. Applicant has shown that cells dissociated from a homogenized whole tumor sample are comparatively more representative of the different types of cells with the whole tumor, e.g. the homogenized whole tumor sample comprises a heterogeneous collection of cells or cell populations including tumor cells, immune cells, stromal cells, etc. (see, for example, PCT Publication Nos. PCT/US2016/060861 and PCT/US2016/060835 the disclosures of which are hereby incorporated by reference herein in their entireties). Likewise, Applicant has shown that residual surgical material from fixed tumors may be blended and dissociated into single cells for further downstream analysis by flow cytometry.

While more representative information is provided, when presented for flow cytometry analysis, the heterogenous populations of cell types (from a homogenate) makes data analysis comparatively more complex. For example, a particular sub-population of cells (e.g. those that are CD8 positive) may be plotted on the same density plot graph with other cell types and if that sub-population represents a minority of the cells within the homogenate, their detection within the heterogeneous mixture may be obscured (see, for example, FIG. 6). And, this is rooted in the fact that flow cytometry is traditionally used to analyze more homogeneous cell populations such as peripheral blood mononuclear cells (PBMCs) (compare FIG. 5A with FIG. 6). As such, is believed that the data presented from flow cytometry for a sample derived from a homogenate may be unfamiliar to the skilled artisan and comparatively more difficult to interpret.

Applicant has developed a method of reducing the complexity of flow cytometry data from a heterogeneous sample derived, for example, from a whole tumor sample. Applicant has developed a method of digital sorting or gating whereby a heterogeneous mixture of tumor cellular particles and normal cellular particles (including immune cells) may be sorted into well-defined populations (e.g. a tumor population or a normal cell population) so as to enhance efficiency in research, tumor analysis, and other downstream processing tasks. The gating strategies described herein provide for substantially homogeneous populations and sub-populations that are easily analyzed, leading to improved data quality and the ability to derive correlations between different subsets of data.

In one aspect of the present disclosure is a method of quantifying a percentage of cells expressing one or more biomarkers comprising: homogenizing a whole tumor sample to provide a homogenized sample; dissociating single cells from the homogenate; staining the cells in the homogenized sample for the presence of the one or more biomarkers; performing at least a first primary gating of the cells in the homogenized sample based on forward scattering (correlated to cell size) and backward scattering (correlated to cell granularity) to provide at least a first population of cells having a first predicted cell type; and determining a percentage of cells expressing a first of the one or more biomarkers in a first sub-population within the first population of cells. In some embodiments, the method does not require a physical sorting step prior to determining the percentage of cells in the at least first sub-population of cells.

In some embodiments, the first predicted cell type are immune cells. In some embodiments, immune cells have a size of less than about 12 μm. In some embodiments, the homogenized tissue sample is further processed prior to staining, wherein the further processing comprises at least one of digesting proteins within the homogenized sample, heating the sample, or filtering the homogenized sample.

In some embodiments, the percentage of cells in the first sub-population expressing the first of the one or more biomarkers is determined by performing a secondary gating of the cells in the first population based on the presence of the first of the one or more biomarkers. In some embodiments, the first of the one or more biomarkers is selected from the group consisting of a CD3, CD4, CD8, CD25, CD163, CD45LCA, CD45RA, and CD45RO cluster of differentiation biomarkers.

In some embodiments, the method further comprises determining a percentage of cells in a second sub-population within the first population of cells expressing a second of the one or more biomarkers, wherein the first and second of the one or more biomarkers are different. In some embodiments, the second of the one or more biomarkers is a cluster of differentiation marker. In some embodiments, the second of the one or more biomarkers is a biomarker other than a cluster of differentiation biomarker. In some embodiments, the second of the one or more biomarkers is selected from the group consisting of PD-1, TIM-3, LAG-3, CD28, CD57, and FOXP3, EPCAM, CK8/18. In some embodiments, the first of the one or more biomarkers is CD3, and the second of the one or more biomarkers is a biomarker which differentiates the immune cells as regulatory T cells, helper T cells, or cytotoxic T cells.

In some embodiments, the method further comprises performing a second primary gating of the cells in the homogenized sample to provide at least a second population of cells having a second predicted cell type. In some embodiments, the second predicted cell type are tumor cells. In some embodiments, the method further comprises determining a percentage of cells within the second population of cells having a chromosomal abnormality. In some embodiments, the method further comprises correlating the determined percentage of cells having the chromosomal abnormality (e.g. aneuploidy) with the determined percentage of cells expressing the first of the one or more biomarkers (e.g. a correlation between cells CD8 positive and aneuploidy).

In some embodiments, the method further comprises making a treatment decision based partially on the determined percentage of cells in the first sub-population expressing the first of the one or more biomarkers.

In another aspect of the present disclosure is a method of quantifying a percentage of cells expressing at least a first biomarker from a plurality of biomarkers in a tissue sample comprising: homogenizing a tissue sample to provide a homogenized sample; staining the cells in the homogenized sample for the presence of the plurality of biomarkers; performing a primary gating of the cells in the homogenized sample based on scattering to provide at least a first population of cells having a first predicted size range; performing at least one secondary gating of the cells in the first population, wherein the at least one secondary gating is based at least on the presence of the first biomarker from the plurality of biomarkers, and wherein the at least one secondary gating provides a first sub-population of cells expressing the first biomarker; and determining a percentage of cells expressing the first biomarker of the plurality of biomarkers in the first sub-population of cells. In some embodiments, the method does not require a physical sorting step prior to determining the percentage of those cells in the first sub-population. In some embodiments, the first population of cells were gated for (i.e. selected) based on their forward and backward scattering (i.e. size and granularity).

In some embodiments, the homogenized sample is stained for at least the presence of a CD3 biomarker. In some embodiments, the homogenized sample is further stained for the presence of at least one additional cluster of differentiation biomarker. In some embodiments, at least one secondary gating is performed based on at least the presence of the CD3 biomarker (e.g. a density plot of forward scattering (FSC) versus CD3 staining intensity). In some embodiments, separate secondary gatings are independently performed based on the presence of the CD3 biomarker and at least one of a CD4 biomarker and/or a CD8 biomarker, to provide a CD3 sub-population, and at least one of a CD4 sub-population and/or a CD8 sub-population. In some embodiments, the percentage of cells in the CD3 sub-population and the at least one of the CD4 and/or CD8 sub-populations are independently determined/quantified.

In some embodiments, the tissue sample is derived from at least one of a whole tumor, a partial tumor, a metastatic tumor, a partial metastatic tumor, or lymph nodes. In some embodiments, the tissue sample is derived from at least one of residual surgical material or a biopsy sample. In some embodiments, the homogenized tissue sample is further processed prior to staining, wherein the further processing comprises at least one of digesting proteins within the homogenized sample, heating the sample, or filtering the homogenized sample.

In some embodiments, the plurality of biomarkers are selected from the group consisting of cluster of differentiation biomarkers, PD-1, TIM-3, LAG-3, and FOXP3. In some embodiments, the cluster of differentiation biomarkers are selected from the group consisting of CD3, CD4, CD8, CD45RA, CD45RO, CD28, and CD57.

In another aspect of the present disclosure is a method of quantifying a percentage of cells expressing at least a first of one or more biomarkers in a homogenized tissue sample comprising: dissociating the homogenized sample into single cells (e.g. including further blending and filtration) to provide a sample made of single cells (e.g. a sample predominantly including single cells); staining the cells for the presence of the one or more biomarkers; probing cells with a flow cytometer; and analyzing the resulting data. In some embodiments, data analysis includes performing at least two sequential gatings to provide at least a first sub-population of cells expressing the first of the one or more biomarkers; and determining a percentage of cells expressing the first of the one or more biomarkers in the first sub-population.

In some embodiments, the at least two sequential gatings comprise a primary gating to provide a first population of cells and a secondary gating to provide the first sub-population of cells. In some embodiments, the primary gating is based on forward scatter and side scatter. In some embodiments, a cutoff is selected for forward and side scatter such that the first population is enriched with immune cells. In some embodiments, a plurality of secondary gatings are conducted.

In some embodiments, secondary gatings are performed for at least two cluster of differentiation biomarkers. In some embodiments, the cluster of differentiation biomarkers are selected from the group consisting of CD3, CD4, CD8, CD45RA, CD45RO, CD28, and CD57. In some embodiments, the method further comprises determining a percentage of cells in a second sub-population of cells expressing a second of the one or more biomarkers, wherein the first and second of the one or more biomarkers are different. In some embodiments, the second of the one or more biomarkers is a biomarker other than a cluster of differentiation marker. In some embodiments, the second of the one or more biomarkers is selected from the group consisting of PD-1, TIM-3, LAG-3, and FOXP3.

The methods of the present disclosure have several clinical applications. In one embodiment, the method can be used to evaluate specific and non-specific immune responses. For example, the method can be used to determine changes in immune function after the development of tumors, to determine a course of treatment for cancer, or to determine whether a treatment being applied is efficacious. Alternatively, the method can be used to determine changes in immune function after treatment of patients with vaccines, immunosuppressants, antiviral agents, antitumor agents or other therapeutics.

BRIEF DESCRIPTION OF THE FIGURES

For a general understanding of the features of the disclosure, reference is made to the drawings. In the drawings, like reference numerals have been used throughout to identify identical elements.

FIG. 11A shows small cells (immune cells) that were sorted (physically separated from the cell mixture), stained for CD3, and then analyzed again by flow cytometry.

FIG. 11B shows physically sorted small cells which were analyzed for the CD3 marker. Here, small cells expressed the CD3 marker as expected.

FIG. 11C illustrates an analysis on the same cell mixture as in FIGS. 11A and 11B, but without gating or sorting.

DETAILED DESCRIPTION

Figure 1:
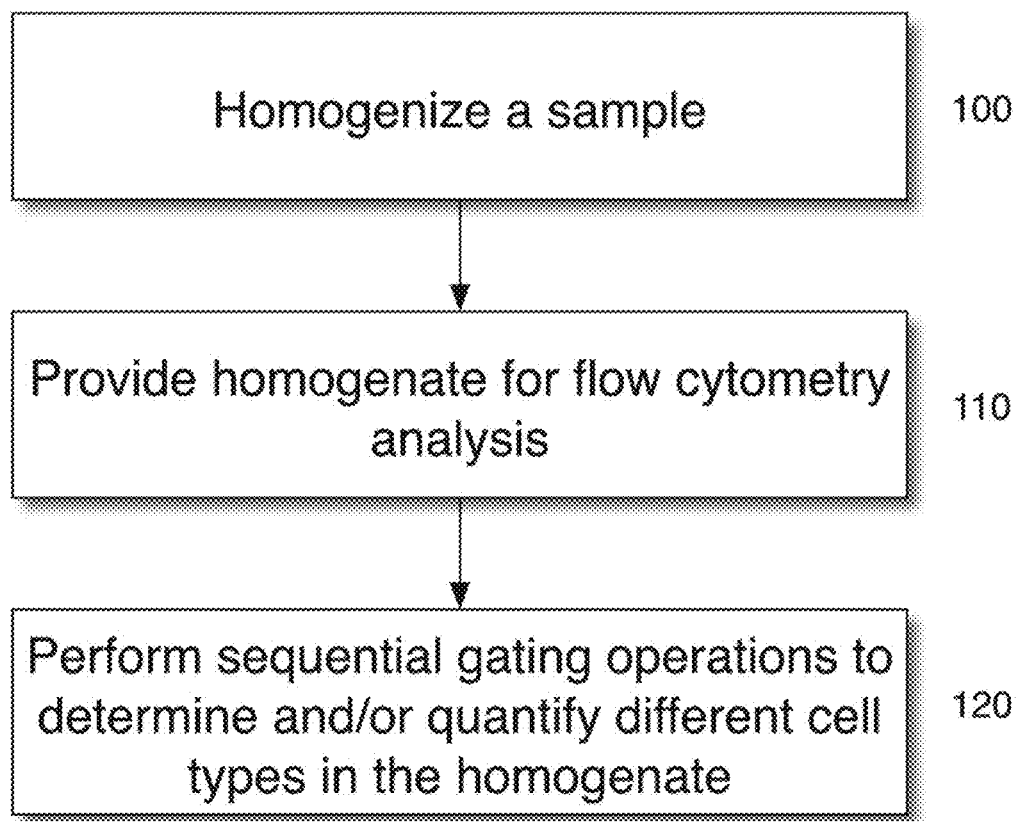
FIG. 1 sets forth a flowchart for quantifying different cells types in a homogenate in accordance with some embodiments of the present disclosure.
Figure 2:
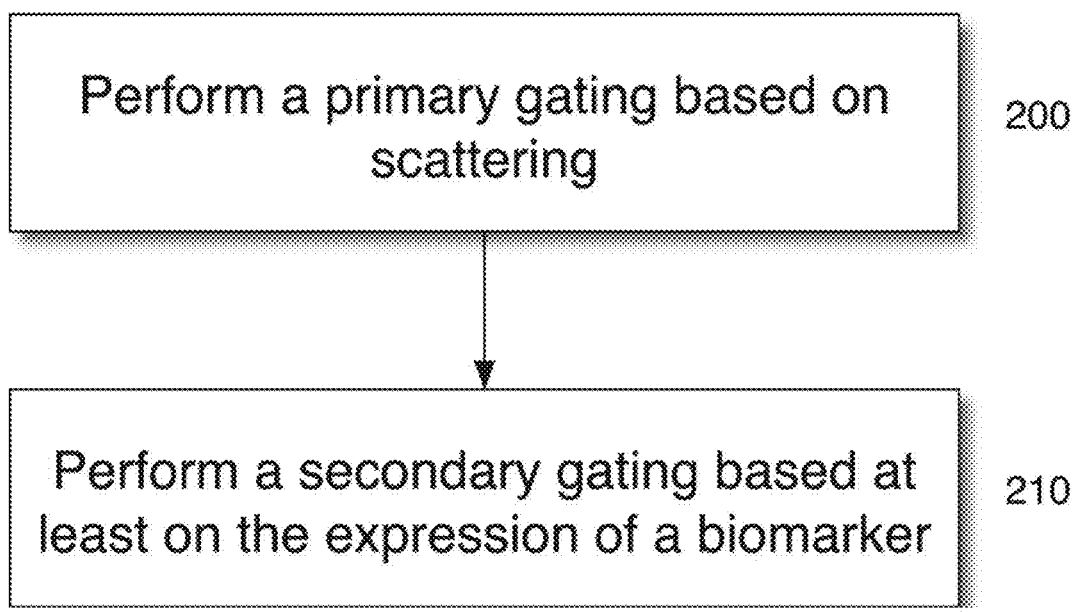
FIG. 2 sets forth a flowchart for performing a sequential gating in accordance with some embodiments of the present disclosure.

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "biological sample," "tissue sample," "specimen" or the like refers to any sample including a biomolecule (such as a protein, a peptide, a nucleic acid, a lipid, a carbohydrate, or a combination thereof) that is obtained from any organism including viruses. Other examples of organisms include mammals (such as humans; veterinary animals like cats, dogs, horses, cattle, and swine; and laboratory animals like mice, rats and primates), insects, annelids, arachnids, marsupials, reptiles, amphibians, bacteria, and fungi. Biological samples include tissue samples (such as tissue sections and needle biopsies of tissue), cell samples (such as cytological smears such as Pap smears or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, cerumen, milk, vaginal fluid, saliva, swabs (such as buccal swabs), or any material containing biomolecules that is derived from a first biological sample. In certain embodiments, the term "biological sample" as used herein refers to a sample (such as a homogenized or liquefied sample) prepared from a tumor or a portion thereof obtained from a subject.

As used herein, the term "biomarker" refers to a biological molecule found in blood, other body fluids, or tissues that is a sign of a normal or abnormal process, or of a condition or disease (such as cancer). A biomarker may be used to determine how well the body responds to a treatment for a disease or condition or if the subject is predisposed to a disease or condition. In the context of cancer, a biomarker refers to a biological substance that is indicative of the presence of cancer in the body. A biomarker may be a molecule secreted by a tumor or a specific response of the body to the presence of cancer. Genetic, epigenetic, proteomic, glycomic, and imaging biomarkers can be used for cancer diagnosis, prognosis, and epidemiology. Such biomarkers can be assayed in non-invasively collected biofluids like blood or serum. Several gene and protein-based biomarkers have already been used in patient care including but, not limited to, AFP (Liver Cancer), BCR-ABL (Chronic Myeloid Leukemia), BRCA1/BRCA2 (Breast/Ovarian Cancer), BRAF V600E (Melanoma/Colorectal Cancer), CA-125 (Ovarian Cancer), CA19.9 (Pancreatic Cancer), CEA (Colorectal Cancer), EGFR (Non-small-cell lung carcinoma), HER-2 (Breast Cancer), KIT (Gastrointestinal stromal tumor), PSA (Prostate Specific Antigen), S100 (Melanoma), and many others. Biomarkers may be useful as diagnostics (to identify early stage cancers) and/or prognostics (to forecast how aggressive a cancer is and/or predict how a subject will respond to a particular treatment and/or how likely a cancer is to recur).

As used herein the term "gating" refers to the selection of a population of particles from a sample, based on the characteristics of the particle. For example, characteristics of a particle can be defined based on the forward scattering (FSC), side scattering (SSC) and/or fluorescence intensity. Therefore, particles with the required characteristics will pass through the gate and are selected for further analysis, while those that do not have the required characteristics will not be selected for further analysis. Digital gating means that certain population are selected to show on a plot after analyzing a mixture of all cells. The selected cell population is "digitally sorted" after analysis of all cells. Physical sorting is the process of removing the selected population from all cells into a separate tube, then analyzing the selected cell population. Both digital sorting and physical sorting are believed to achieve analysis of certain cell populations as described herein.

As used herein, the term "homogenizing" refers to a process whereby a biological sample is brought to a state such that all fractions of the sample are equal in composition. In the present disclosure, the "homogenization" will in general preserve the integrity of the majority of the cells within the sample, e.g., at least 50, 80, 85, 90, 95, 96, 97, 98, 99, 99.9% or greater percentage of the cells in the sample will not be ruptured or lysed as a result of the homogenization process. The homogenates may be substantially dissociated into individual cells (or clusters of cells) and the resultant homogenate or homogenates are substantially homogeneous (consisting of or composed of similar elements or uniform throughout).

As used herein, the terms "label" or "stains" mean a reagent that is capable of binding to an analyte, being internalized or otherwise absorbed, and being detected, e.g., through shape, morphology, color, fluorescence, luminescence, phosphorescence, absorbance, magnetic properties, or radioactive emission. Likewise, the terms "labeling," "staining," or the like as used herein generally refers to any treatment of a biological specimen that detects and/or differentiates the presence, location, and/or amount (such as concentration) of a particular molecule (such as a lipid, protein or nucleic acid) or particular structure (such as a normal or malignant cell, cytosol, nucleus, Golgi apparatus, or cytoskeleton) in the biological specimen. For example, staining can provide contrast between a particular molecule or a particular cellular structure and surrounding portions of a biological specimen, and the intensity of the staining can provide a measure of the amount of a particular molecule in the specimen. Staining can be used to aid in the viewing of molecules, cellular structures and organisms not only with bright-field microscopes, but also with other viewing tools, such as phase contrast microscopes, electron microscopes, and fluorescence microscopes. Some staining performed by the system can be used to visualize an outline of a cell. Other staining performed by the system may rely on certain cell components (such as molecules or structures) being stained without or with relatively little staining other cell components. Examples of types of staining methods performed by the system include, without limitation, histochemical methods, immunohistochemical methods, and other methods based on reactions between molecules (including non-covalent binding interactions), such as hybridization reactions between nucleic acid molecules. Particular staining methods include, but are not limited to, primary staining methods (e.g., H&E staining, Pap staining, etc.), enzyme-linked immunohistochemical methods, and in situ RNA and DNA hybridization methods, such as fluorescence in situ hybridization (FISH).

As used herein, the terms "representative sample" and "representative sampling" as used herein refer to a sample (or a subset of a sample) that accurately reflects the components of the entirety and, thus, the sample is an unbiased indication of the entire population. In general, this means that the different types of cells and their relative proportion or percentages within the representative sample or a portion thereof essentially accurately reflects or mimics the relative proportion or percentages of these cell types within the entire tissue specimen, generally a solid tumor or portion thereof. As used herein, "sequencing" or "DNA sequencing" refers to biochemical methods for determining the order of the nucleotide bases, adenine, guanine, cytosine, and thymine, in a DNA oligonucleotide. Sequencing, as the term is used herein, can include without limitation parallel sequencing or any other sequencing method known of those skilled in the art, for example, chain-termination methods, rapid DNA sequencing methods, wandering-spot analysis, Maxam-Gilbert sequencing, dye-terminator sequencing, or using any other modern automated DNA sequencing instruments.

As used herein, the term "tumor" refers to a mass or a neoplasm, which itself is defined as an abnormal new growth of cells that usually grow more rapidly than normal cells and will continue to grow if not treated sometimes resulting in damage to adjacent structures. Tumor sizes can vary widely. A tumor may be solid or fluid-filled. A tumor can refer to benign (not malignant, generally harmless), or malignant (capable of metastasis) growths. Some tumors can contain neoplastic cells that are benign (such as carcinoma in situ) and, simultaneously, contain malignant cancer cells (such as adenocarcinoma). This should be understood to include neoplasms located in multiple locations throughout the body. Therefore, for purposes of the disclosure, tumors include primary tumors, lymph nodes, lymphatic tissue, and metastatic tumors.

As used herein, the term "tumor sample" encompasses samples prepared from a tumor or from a sample potentially comprising or suspected of comprising cancer cells, or to be tested for the potential presence of cancer cells, such as a lymph node.

Separation of Cells and/or Nuclei from Tissue

Figure 3:
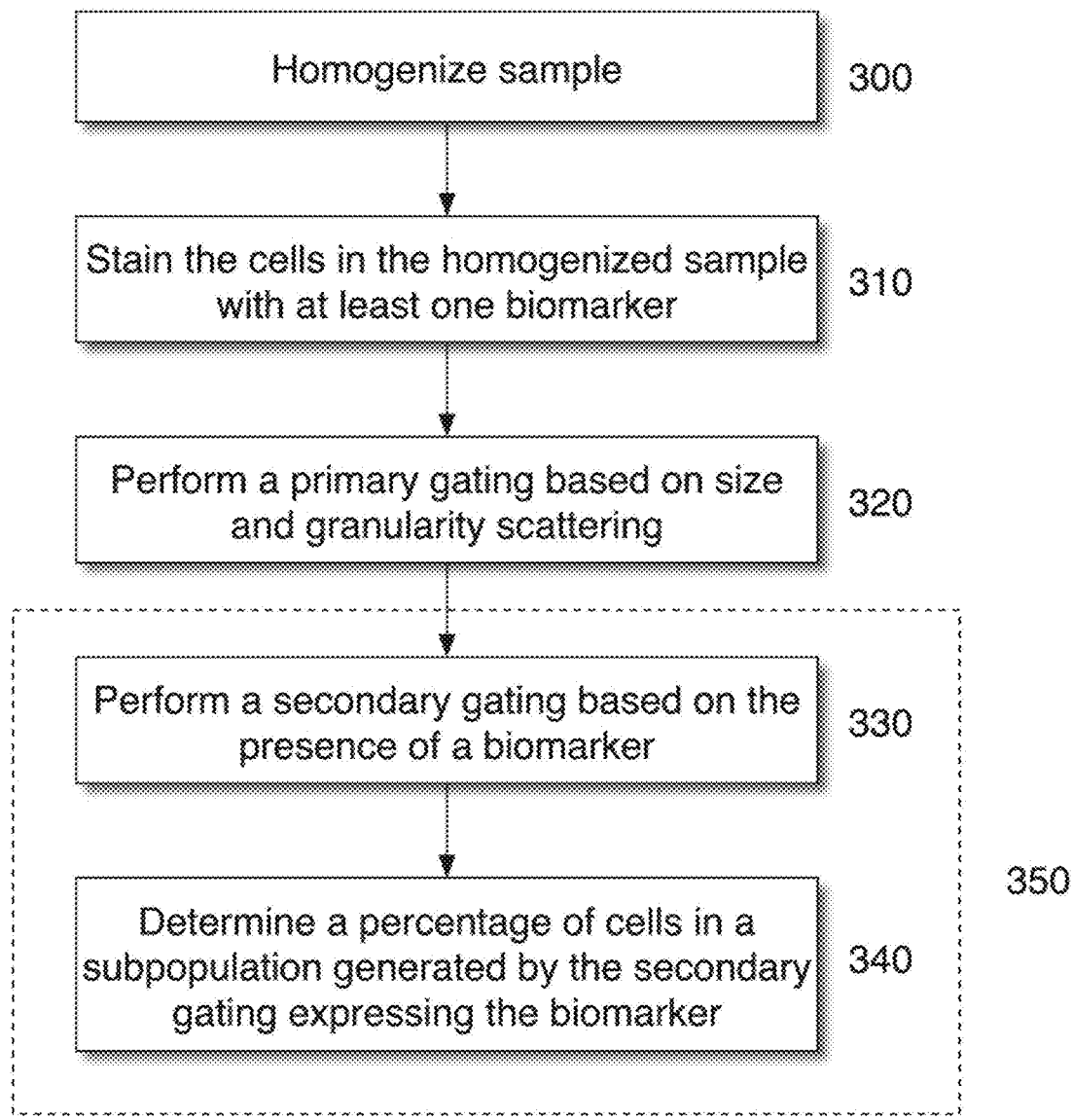
FIG. 3 sets forth a flowchart for quantifying different cells types in a homogenate in accordance with some embodiments of the present disclosure.

With reference to FIGS. 1 and 3, in some embodiments, cells, nuclei, and/or small tissue aggregates are separated from a sample, such as a tissue sample. In some embodiments, the cells, nuclei, and/or small tissue aggregates are separated from the tissue sample by homogenizing the tissue sample (step 100). In some embodiments, the cells, nuclei, and/or small tissue aggregates present in the homogenized sample are then presented for flow cytometry analysis (step 110). The dissociated cells, nuclei, and/or small tissue aggregates may then be gated (step 120) and then further analyzed.

In some embodiments, the tissue sample for homogenization (step 100) is derived from a tumor (cancerous or non-cancerous), a metastatic lesion, normal tissue, whole blood, or a lymph node. In some embodiments, the tissue sample is a residual surgical sample, a biopsy sample, or a histological sample. In some embodiments, the tissue sample is a fresh sample, namely one that has not been preserved. In some embodiments, the tissue sample is a fixed tissue sample. In some embodiments, the tissue sample is derived from a formalin-fixed paraffin-embedded tissue block. In some embodiments, multiple tissue sources may be combined and then the cells and/or nuclei separated from the collective tissue samples.

Homogenization of Tissue Samples

In some embodiments, a tumor sample, lymph node sample, and/or other tissue sample is homogenized (step 300) by placing the sample into a mechanical shearing apparatus, e.g. a blender or an ultra sonicator. The homogenization produces a range of tissue fragments. Methods of preparing homogenized tumor samples or lymph node samples are disclosed in PCT Application No. PCT/US2016/060861, the disclosure of which is hereby incorporated by reference herein in its entirety.

Following sufficient mechanical shearing to disassociate the tumor, lymph node, and/or other tissue sample, all the subpopulations of tumor cells that were originally spatially segregated within the original sample are distributed throughout the newly homogenized sample. That is, as a result of homogenizing a tumor, one or more lymph nodes, or any combination thereof, any heterogeneity of cells within the tumor is substantially homogeneously (uniformly) distributed within the resultant homogenate or a portion or fraction thereof, such that the homogenate (or any fraction thereof) substantially homogeneously expresses the heterogeneity of the tumor and/or lymph node sample which was the input. By homogenizing tumors and/or lymph nodes to generate a sample (or homogenate) that is representative of the tumor in its entirety, it is possible, in some embodiments, to characterize the landscape (such as the heterogeneity) of the tumor, e.g. it may be possible to analyze each of the different populations of cells or nuclei contained throughout the homogenate (e.g. to determine a quantity of a specific type of immune cell so as to determine whether a patient is a candidate for a particular type of treatment). In some embodiments, the methods are useful for detecting tumor infiltrating lymphocytes, such as the relative abundance of different tumor infiltrating lymphocytes.

Dissociation of Cells, Nuclei, and/or Small Tissue Aggregates from Tumors

The homogenized samples (from step 200) may be further dissociated and/or treated to provide dissociated cells, nuclei, and/or small tissue aggregates (step 210). In general, there are three primary methods for tissue dissociation including enzymatic dissociation, chemical dissociation and mechanical dissociation or any combination thereof. The selection of a method for dissociation is usually made based on the tissue type and tissue origin.

Enzymatic dissociation is the process of using enzymes to digest tissue pieces thereby releasing cells from tissue. Many different types of enzymes may be used in this process and, as the skilled artisan will appreciate, certain enzymes are more effective with certain tissue types. The skilled artisan will also appreciate any enzymatic dissociation process may use one or more enzymes in combination with each other, or one or more enzymes in combination with other chemical and/or mechanical dissociation methods. Examples of suitable enzymes include, but are not limited to, collagenase, trypsin, elastase, hyaluronidase, papain, DNase I, neutral protease, and trypsin inhibitor.

Collagenase is a proteolytic enzyme used to digest proteins found in the extracellular matrix. Unique to enzymatic proteases, collagenase can attack and degrade the triple-helical native collagen fibrils that are commonly found in connective tissue. There exist four basic collagenase types, namely: Type 1, which is suitable for use in epithelial, liver, lung, fat and adrenal tissue cell specimens; Type 2, which is suitable for use in heart, bone, muscle, thyroid and cartilage tumor originating tissues given its high proteolytic activity; Type 3, which is suitable for use in mammary cells given its low proteolytic activity; and Type 4: which is suitable for islets and other research protocols where receptor integrity is important, given its tryptic activity.

Trypsin is described as a pancreatic serine (an amino acid) protease that has specificity for peptide bonds that involve the carboxyl group of arginine and lysine amino acids. It is considered one of the most highly specific proteases. Trypsin alone is not usually effective for tissue dissociation because it shows minimal selectivity to extracellular proteins. It is usually combined with other enzymes such as collagenase or elastase.

Elastase is another pancreatic serine protease, which has specificity for peptide bonds that are next to neutral amino acids. It is unique among proteases in its ability to hydrolyze native elastin. Elastase can also be found in blood components and bacteria. In some embodiments, it is suitable for isolation of Type II cells from lung tissue.

Hyaluronidase is a polysaccharidase, this enzyme is often used for dissociation of tissues, typically when combined with a more crude protease such as collagenase. It has affinity for bonds found in just about all connective tissues.

Papain is a sulfhydryl protease, it has wide specificity and so can degrade most protein substrates more thoroughly than pancreatic proteases, i.e. trypsin or elastase. Papain is frequently used to isolate neuronal materials from tissues.

Deoxyribonuclease I (DNase I) is frequently included in enzymatic cell isolation procedures to digest nucleic acids that leak into the dissociation medium and can increased viscosity and recovery problems. Without wishing to be bound by any particular theory, it is believed that DNaseI will not damage intact cells.

Neutral protease, such Dispase® (available from Worthington Biochemical), is a bacterial enzyme with mild proteolytic activity, Dispase® is useful for isolating primary and secondary cell cultures because of its ability to maintain cell membrane integrity. It has been found to more efficiently dissociate fibroblast-like cells as compared to epithelial-like cells. It is inhibited by EDTA.

A trypsin inhibitor is derived mainly from the soybean, it inactivates trypsin, and so is sometimes used for specific cell isolation protocols.

Chemical dissociation takes advantage of the fact that cations participate in the maintenance of intracellular bonds and the intracellular matrix. By introducing EDTA or EGTA, which binds these cations, the intercellular bonds are disrupted, thereby allowing for dissociation of the tissue structures.

Lastly, mechanical dissociation requires cutting, scraping or scratching the tissue into small pieces, then the minced-up tissue is washed in medium in order to separate the cells from the tissue and sometimes gentle agitation and/or sonication are also used to help loosen the cells. In other embodiments, mechanical dissociation may involve homogenizing a sample, as described further herein.

In some embodiments, cells within the homogenized sample, or filtered homogenized sample, are lysed to release cellular components. For example, cells may be lysed using a French press or similar type of lysis apparatus, microfluidizers, grinding, milling, chemical or enzymatic lysis (including those described above), and/or using other techniques known in the art. In some embodiments, membrane lipids and proteins (include histones) are removed from the sample containing the cellular components (e.g. by adding surfactants or enzymes (proteases)).

Further processing of the homogenized, representative, or dissociated samples into individual nuclei requires the removal of the cell membrane. Current nuclear isolation methods for fresh cells do not require enzymes to liberate nuclei, and nuclear isolation from formalin fixed sample is not a common method. To efficiently isolate individual nuclei, while maintaining cytoskeletal markers that would enable differentiation between normal and tumor nuclei, enzymes (e.g. pronase, proteinase K, pepsin, trypsin, Accumax, collagenase H) may be used to reveal nuclei without undue damage that would liberate DNA from the treated nuclei. Particular methods of isolating nuclei from a homogenate or a representative sample are disclosed in co-pending PCT Application No. PCT/US2016/060861, the disclosure of which is hereby incorporated by reference herein in its entirety.

In some embodiments, the homogenate is further blended with a typical blender (IKA blender) then filtered with set of cell strainers of different sizes (e.g. about 20 um, about 10 um, etc.). In some embodiments, a metal mesh is used to remove large tissue fragments before filtration with cell strainers. In some embodiments, the obtained sample is predominantly composed of single cells (some small cell aggregated such as doublets) that can be stained for with desired markers.

Staining of Cells within the Homogenized Sample

Figure 12:
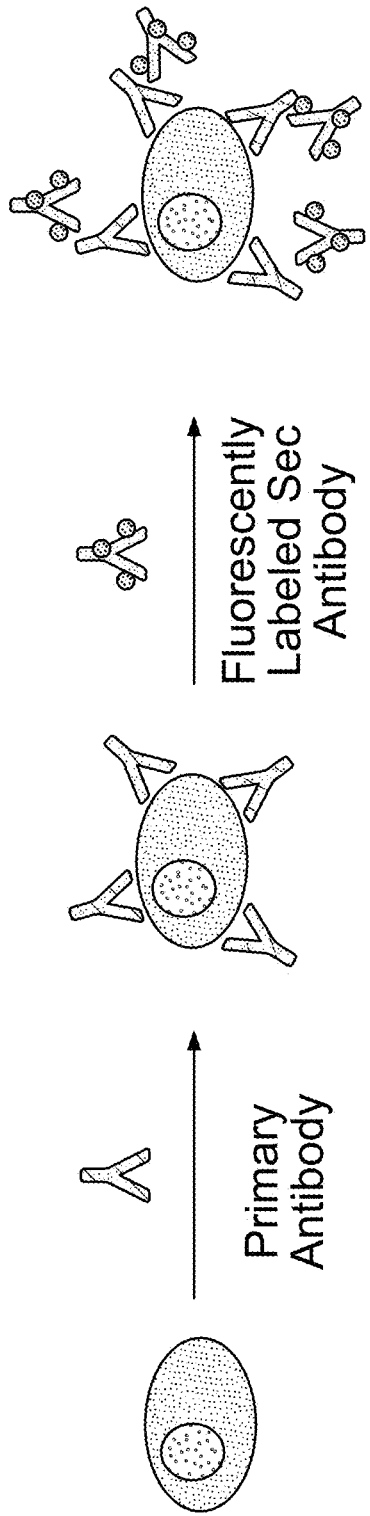
FIG. 12 illustrates methods of staining cells derived from a homogenized sample.
Figure 12:
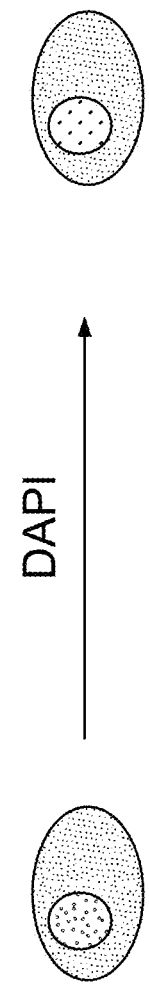

In some embodiments, the dissociated cells and/or nuclei are labelled or stained prior to evaluating the sample by flow cytometry so that different cell types can be identified (see, for example, FIG. 12). The label or stain can be any detectable label or reporter moiety that can identify different cell types by flow cytometry, for example a fluorescent label (step 310 of FIG. 3).

In some embodiments, the homogenized sample is contacted with one or more detection probes, which may be visualized by applying one or more detection reagents (see, for example, PCT Publication No. WO/2017/085307, the disclosure of which is hereby incorporated by reference herein in its entirety). For example, in some embodiments, the detection probes utilized are specific for immune cell markers. In some embodiments, the detection probes are selected from primary antibodies that are specific for markers of lymphocytes, including T lymphocytes and B lymphocytes. In other embodiments, the detection probes are selected from primary antibodies that are specific for markers of leukocytes, T-helper cells, T-regulatory cells, and/or cytotoxic T cells. In yet other embodiments, the detection probes are selected from primary antibodies that are specific for a broad-spectrum lymphocyte secondary biomarker.

In some embodiments, antibodies can be conjugated to different fluorescent dyes by any conventional procedure, as, for example, the procedures described by Wofsy et al., "Modification and Use of Antibodies to Label Cell Surface Antigens, "Selected methods in Cellular Immunology, B. B. Mishell and S. M. Siigi, ed., W. H. Freeman and Co. (1980). For example, different types of immune cells can be determined using fluorescent labelled antibodies specific for antigens on the different cell types. Examples of fluorescent labelled antibodies specific for different cell types include, but are not limited to, CD3 FITC/CD16+CD56PE for NK cells; CD3 FITC/CD19PE for B cells; CD45 FITC/CD14PE for monocytes; CD3 FITC/CD4PerCP for T helper cells; CD3 FITC/CD8PE for CD8 cells; CD4PerCP/CD45 RO PE for T helper memory cells; CD8 FITC/CD45RO PE for CD8 memory cells; CD62 FITC/CD45RA PE/CD4PerCP for naive T helper cells; CD62 FITC/CD45RA PE/CD8PerCP for naive CD8 cells. In other embodiments, the cells or nuclei are stained with 4',6-diamidino-2-phenylindole (DAPI).

In some embodiments, the detection probes are selected from primary antibodies that are specific for certain receptors and/or ligands including, but not limited to, CD45, CD45LCA (where 'LCA' refers to leukocyte common antigen) CD3, CD4, CD8, CD20, CD 25, CD19 and CD163 (e.g. anti-CD antibodies). In other embodiments, the detection probe is a primary antibody that is specific for CD45LCA. In some embodiments, the detection probe is anti-CD45LCA primary antibody, such as available from Ventana Medical Systems, Tucson, AZ, and available under the brand name CONFIRM anti-CD45, LCA (RP2/18) (a mouse monoclonal antibody (IgGI) that specifically binds to antigens located on the membranes of leukocytes).

In some embodiments, the samples are stained for the presence of at least a lymphocyte marker. Lymphocyte markers include CD3, CD4, and CD8. In general, CD3 is the "universal marker" for T cells. In some embodiments, further analysis (staining) is performed to identify a specific type of T cell, e.g. regulatory, helper, or cytotoxic T cell. For example, CD3+ T-cells can be further distinguished as being cytotoxic T-lymphocytes positive for the CD8 biomarker (CD8 is a specific marker for cytotoxic T lymphocytes). CD3+ T cells can also be distinguished as being cytotoxic T-lymphocytes positive for Perforin (Perforin is a membranolytic protein that is expressed in the cytoplasmic granules of cytotoxic T cells and natural killer cells). Cytotoxic T cells are effector cells that actually "kill" tumor cells. They are believed to act by direct contact to introduce the digestive enzyme granzyme B into the tumor cell cytoplasm, thereby killing it. Similarly, CD3+ T cells can be further distinguished as regulatory T cells positive for the FOXP3 biomarker. FOXP3 is a nuclear transcription factor that is the most specific marker for regulatory T cells. Likewise, CD3+ T cells may be further distinguished as helper T cells positive for the CD4 biomarker.

In view of the foregoing, in some embodiments the homogenized sample may be stained for one or more immune cell markers including at least CD3 or total lymphocytes as detected by hematoxylin & eosin staining. In some embodiments, at least one additional T cell specific marker may also be included, such as CD8 (marker for cytotoxic T-lymphocytes), CD4 (marker for helper T-lymphocytes), FOXP3 (marker for regulatory T-lymphocytes), CD45RA (marker for naive T-lymphocytes), and CD45RO (marker for memory T-lymphocytes). In one specific embodiment, at least two markers including human CD3 (or total lymphocytes as detected by H&E staining) and human CD8 are used.

In some embodiments, T-cells, for example CD8-positive cytotoxic T-cells, can be further distinguished by a variety of biomarkers that include PD-1, TIM-3, LAG-3, CD28, and CD57. As such, in some embodiments, T-cells are stained with at least one of a variety of lymphocyte biomarkers (e.g., CD3, CD4, CD8, FOXP3) for their identification, and additional biomarkers (LAG-3, TIM-3, PD-L1, etc.) for further differentiation.

Gating of Cell Populations

Following the separation of cells, nuclei, and/or small tissue aggregates from a tissue sample or, more specifically, following the homogenization (step 300) and staining of cells, nuclei, and/or small tissue aggregates (step 310), the cells, nuclei, and/or small tissue aggregates are provided for flow cytometry analysis. In some embodiments, the sample is electronically or virtually sorted (step 120 of FIG. 1; steps 320 and 330 of FIG. 3).

In some embodiments, flow cytometry data from a homogenized sample (e.g. a population of all cells dissociated from a whole tumor comprising immune cells, tumor cells, epithelial cells) is believed to have a "low quality" due to the nature of the heterogeneous cell population being analyzed. This heterogeneous population of analyzed cells is made of cells having different sizes and granularities that are not "organized" in distinct populations as "typical" in flow cytometry data. Since flow cytometry analysis is based mainly on looking at distinct cell populations on a dot plot, data from homogenized samples would is believed to look "odd" as no distinct cell population could be defined. When gating is performed for small cells, a more homogeneous cell population (e.g. immune cells which have similar size and granularity leading to distinct population on the dot plot) is able to be analyzed and, as a result, the data would then appear like more like conventional flow cytometry data (e.g. distinct populations) and the increase in fluorescence due to the staining of a certain sub-population of the immune cell population may be easier to depict. This process of gating does not change the data, i.e. it only depicts it in a way that flow cytometry users find themselves familiar with. The gating process allows one to look at certain cell population (e.g. immune cells) even though a mixture of all cells in a sample is analyzed. Therefore, the resulting selected cell population is more homogeneous in size and granularity and presents as distinct cell populations on a flow cytometry data plot.

In some embodiments, the present disclosure provides a gating scheme whereby a homogenized mixture of cells or nuclei are first gated based on size (a primary gating) (step 200) to provide a first population of cells or nuclei having a first size range or predicted cell type; and then gated a second time (a secondary gating) based at least on the expression of a biomarker (step 210). The primary and/or secondary gatings may each be performed once or multiple times.

Figure 5A:
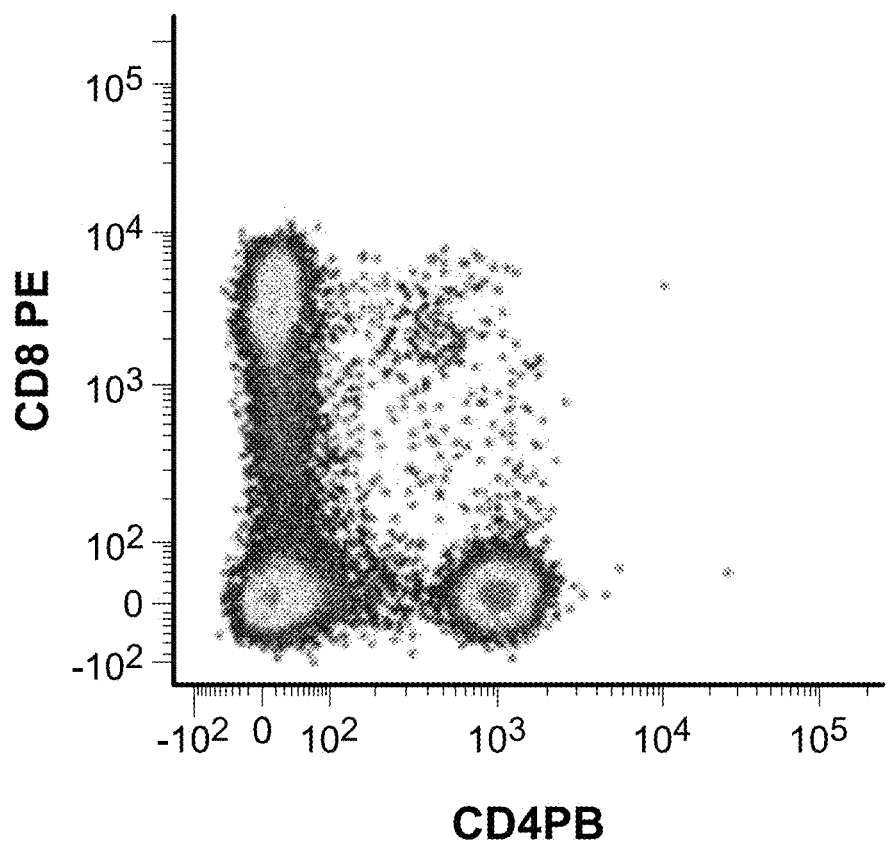
FIG. 5A illustrates a CD8 versus CD4 density plot clearly illustrating populations of CD4 and CD8 cells, the sample being derived from a fresh lymphocyte sample. The figure illustrates how flow cytometry data shows distinct populations (CD4 positive, CD8 positive and double negative) in a dot plot. The illustrated data is from the analysis of immune cells only (a homogeneous population) from fresh blood (it is not a cell mixture).
Figure 5B:
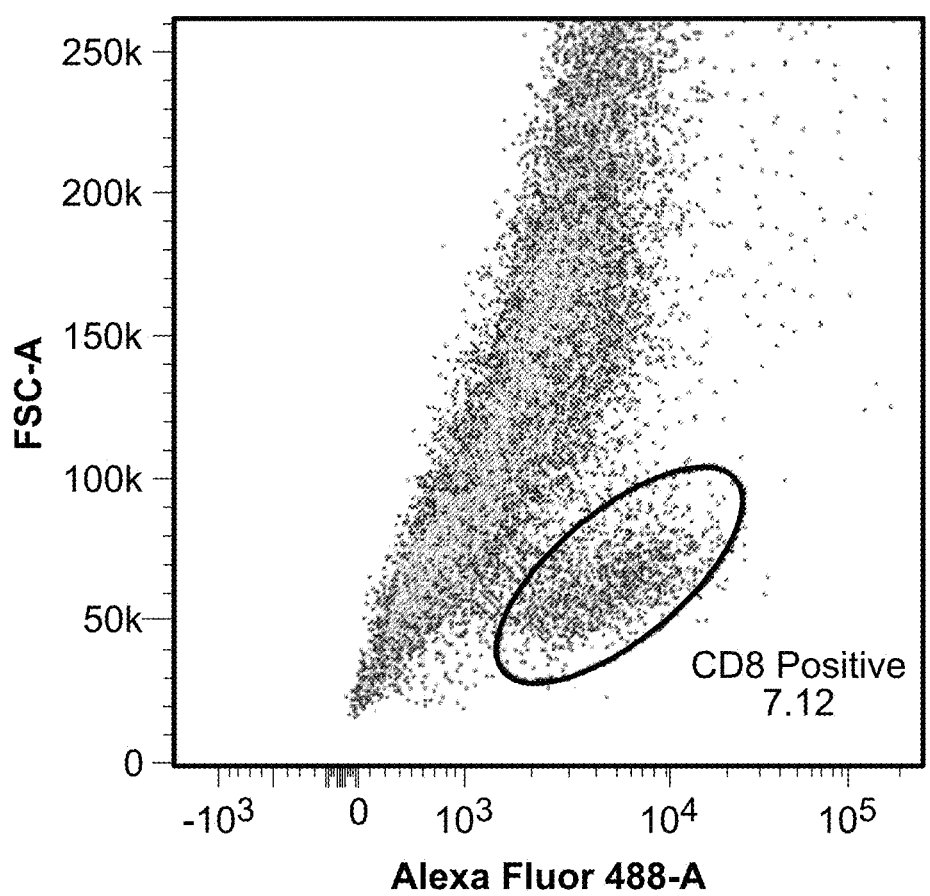
FIG. 5B illustrates a FSC versus CD8 density plot illustrating the gating of a population of CD8 cells. This figure shows flow cytometry analysis of dissociated cells from a whole tumor (e.g. very heterogeneous population made of immune, tumor, epithelial cells). No distinct cell population (round circles in the dot plot of FIG. 5A) is shown in FIG. 5B which makes the data more difficult to be accepted by flow cytometry users.
Figure 6A:
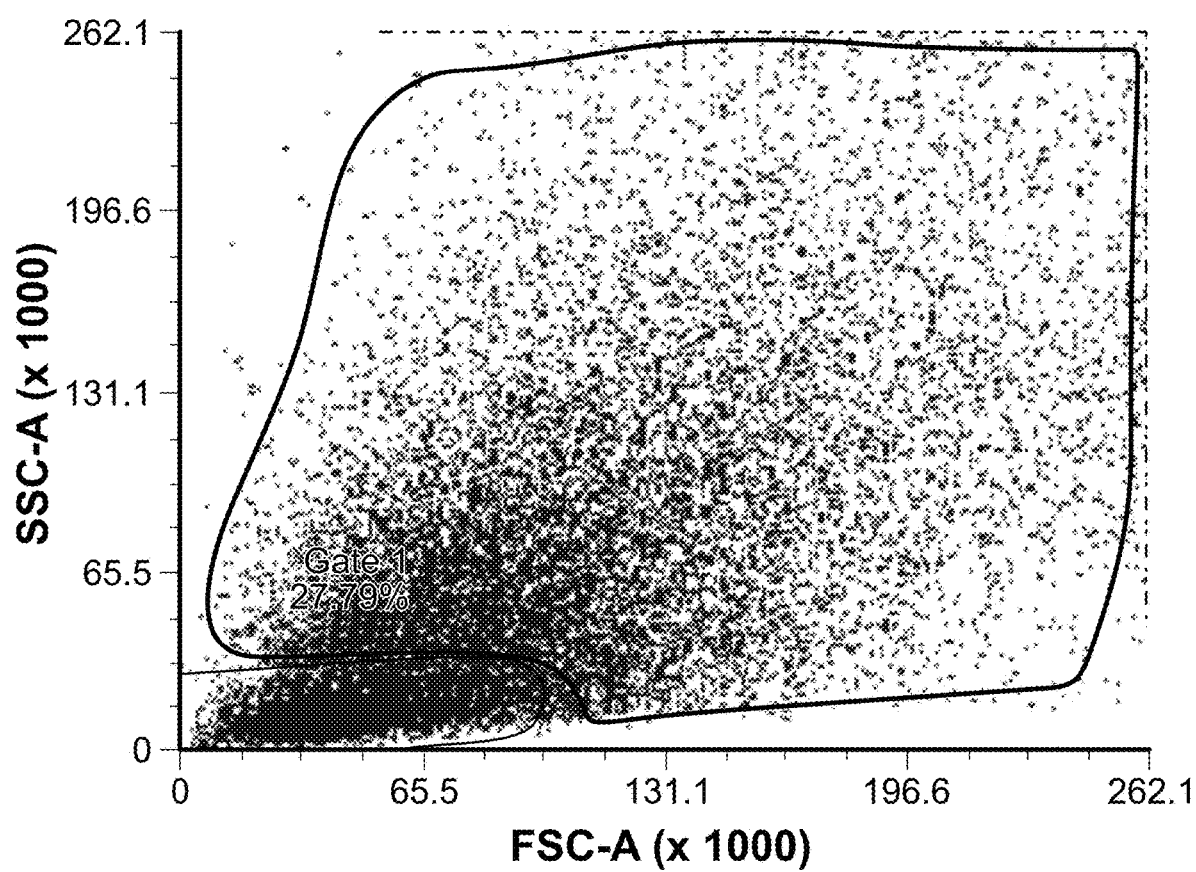
FIG. 6A illustrates a density plot (FSC versus SSC (side scattering)) of a filtered homogenate, where two gatings are selected based on scattering. All filtered cells from the homogenate are illustrated.
Figure 6B:
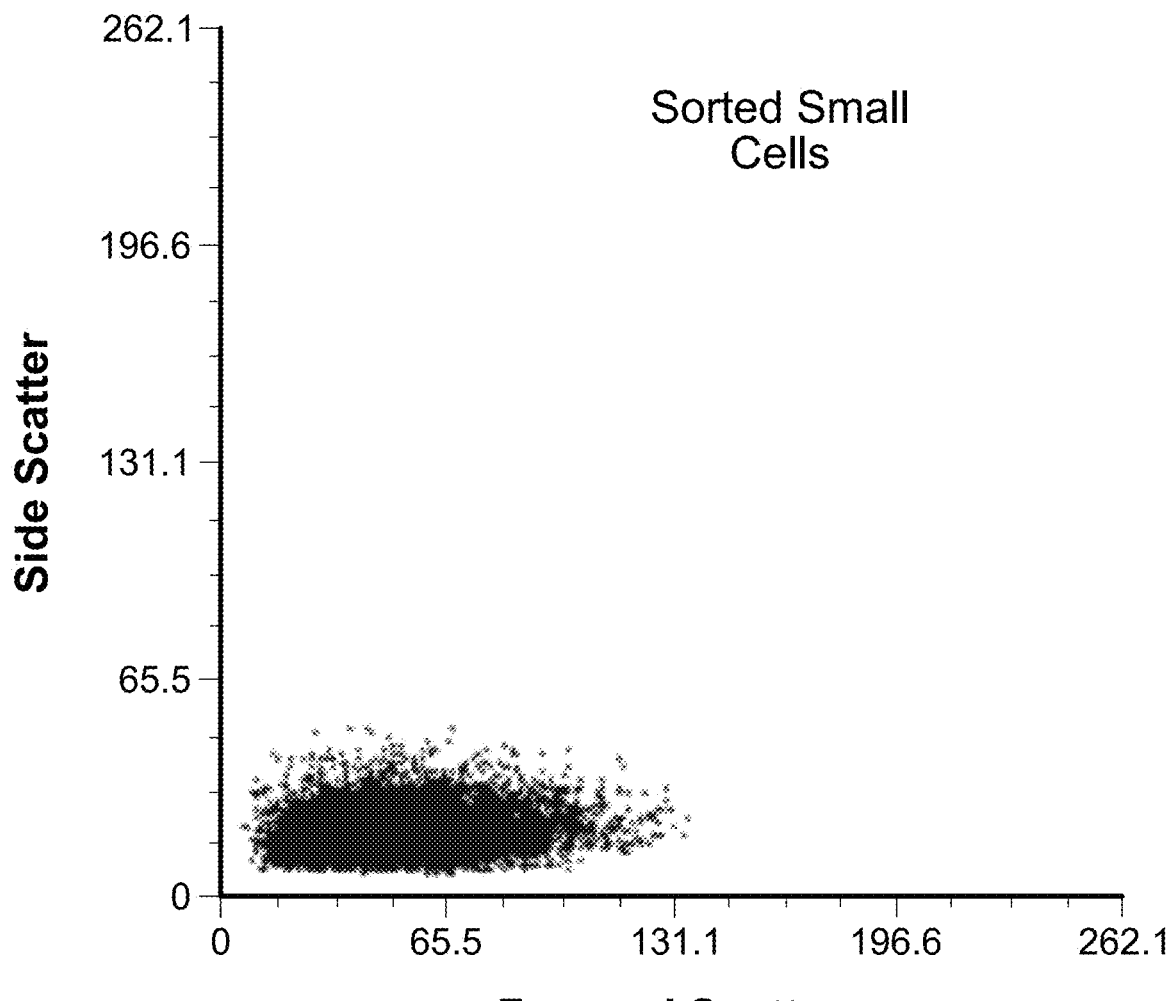
FIG. 6B illustrates a density plot (FSC versus SSC) of a filtered homogenate after primary gating, where just the digitally sorted small cells remain.

In some embodiments, a primary gating is performed to distinguish one or more populations of cells based on forward scattering (FSC) and side scattering (SSC) properties. It is believed that forward and side scatter provide an estimation of the size and granularity of the cells, respectively, although this can depend on several factors such as the sample, the wavelength of the laser, the collection angle and the refractive index of the sample and the sheath fluid. In some embodiments, distinguishing populations of cells can be more straight forward for cell lines where there is only one type of cell (see FIG. 5A), but it can be more complex for samples where there are multiple cell types, such as in a homogenized tissue sample, i.e. cell heterogeneity in the homogenized sample significantly reduces the quality of flow cytometry data (compare FIG. 5A with FIG. 5B). FIGS. 5A and 5B show stained samples, whereas FIGS. 6A and 6B show forward vs. side scatter (no markers shown).

In embodiments where the homogenized sample is derived from a tumor sample, the skilled artisan will appreciate that the homogenized sample will contain a population of tumor cells and populations of other cells, such as immune cells. Applicant has previously shown that such populations of cells may be physically sorted (see PCT Application No. PCT/EP2018/058809 the disclosure of which is hereby incorporated by reference herein in its entirety). The skilled artisan will appreciate that a gating strategy based on scattering may be utilized to digitally sort those cells in a tumor cell population from those cells in other populations present within the homogenized sample.

In some embodiments, such a primary gating strategy enables the selection of cells having a particular predicted size range (e.g. a size from between about 3 μm to about 6 μm) or predicted cell type (e.g. immune cells). In some embodiments, the relative proportion of cells having a first size (e.g. tumor cells having a size greater than 12 μm) and a second size (e.g. immune cells having a size greater less 12 μm) may be determined and/or quantified by placing gates in the areas of the density plots where the different populations would be estimated or predicted to be. For example, if it is desired to determine percentages of different types of immune cells within a homogenized tumor sample, an operator can select a primary gating trace that takes into account the properties of such immune cells as they differ from tumor cells, e.g. the size differences between immune and tumor cells.

Figure 4:
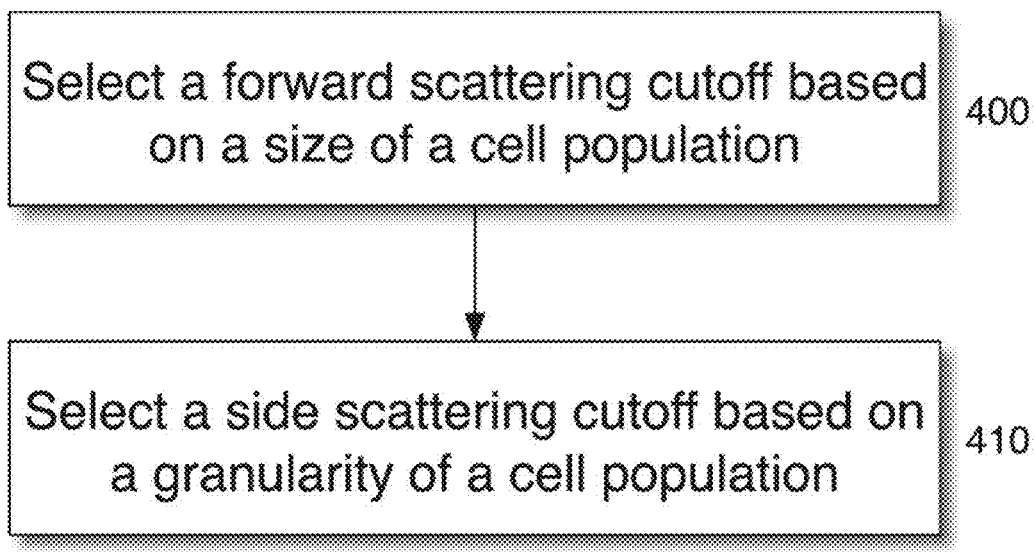
FIG. 4 sets forth a flowchart illustrating the steps of selecting a gate size in accordance with some embodiments of the present disclosure.

As illustrated in the two-parameter density plot of FIG. 6, a primary gating strategy (step 200 or step 330) may be selected such that small cells may be segregated from large cells, including tumor cells, based on forward and side scattering. As illustrated in FIG. 6, comparatively smaller immune cells may be digitally separated from larger tumor cells, both being present in the homogenized tumor sample, by tracing a gate onto the two-parameter density plot of FSC versus SSC (the gate estimating the physical properties of the immune cells relative to the other cells in the sample). In some embodiments, given that immune cells are comparatively smaller than tumor cells, an upper limit to the gate trace on the forward scatting axis is selected such that the population of cells generated after primary gating is enriched with the smaller immune cells (see step 400 of FIG. 4). Likewise, given that immune cells have less complexity and therefore less granularity than tumor cells, an upper limit of side scattering is selected to provide a population enriched with those cells having reduced granularity as compared with tumor cells (see step 410 of FIG. 4).

Figure 8A:
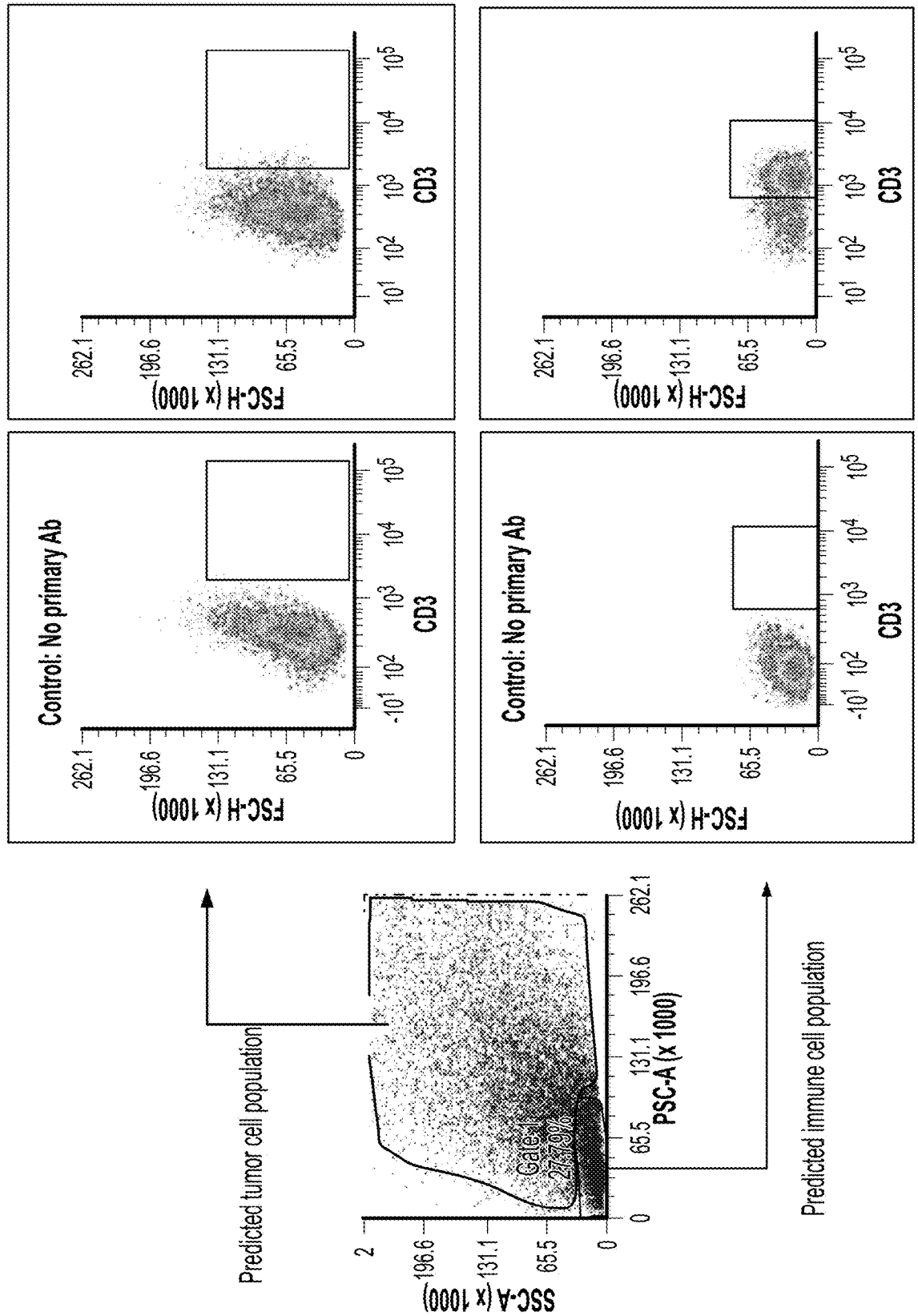
FIG. 8A illustrates the analysis of gated large cells for the CD3 marker (top two panels). The upper right panel shows the control, where no primary antibody was added and the upper left panel shows the actual sample. The rectangle in each panel shows where the positive cells (CD3 positive cells) should be located. Large cells did not show any CD3 positivity, which was expected since the large cells are mostly tumor cells which do not express the CD3 marker. The bottom panels show the analysis of the small cells for the same CD3 marker. Most of the small cells did express CD3, which was expected since the small cells were immune cells.
Figure 8B:
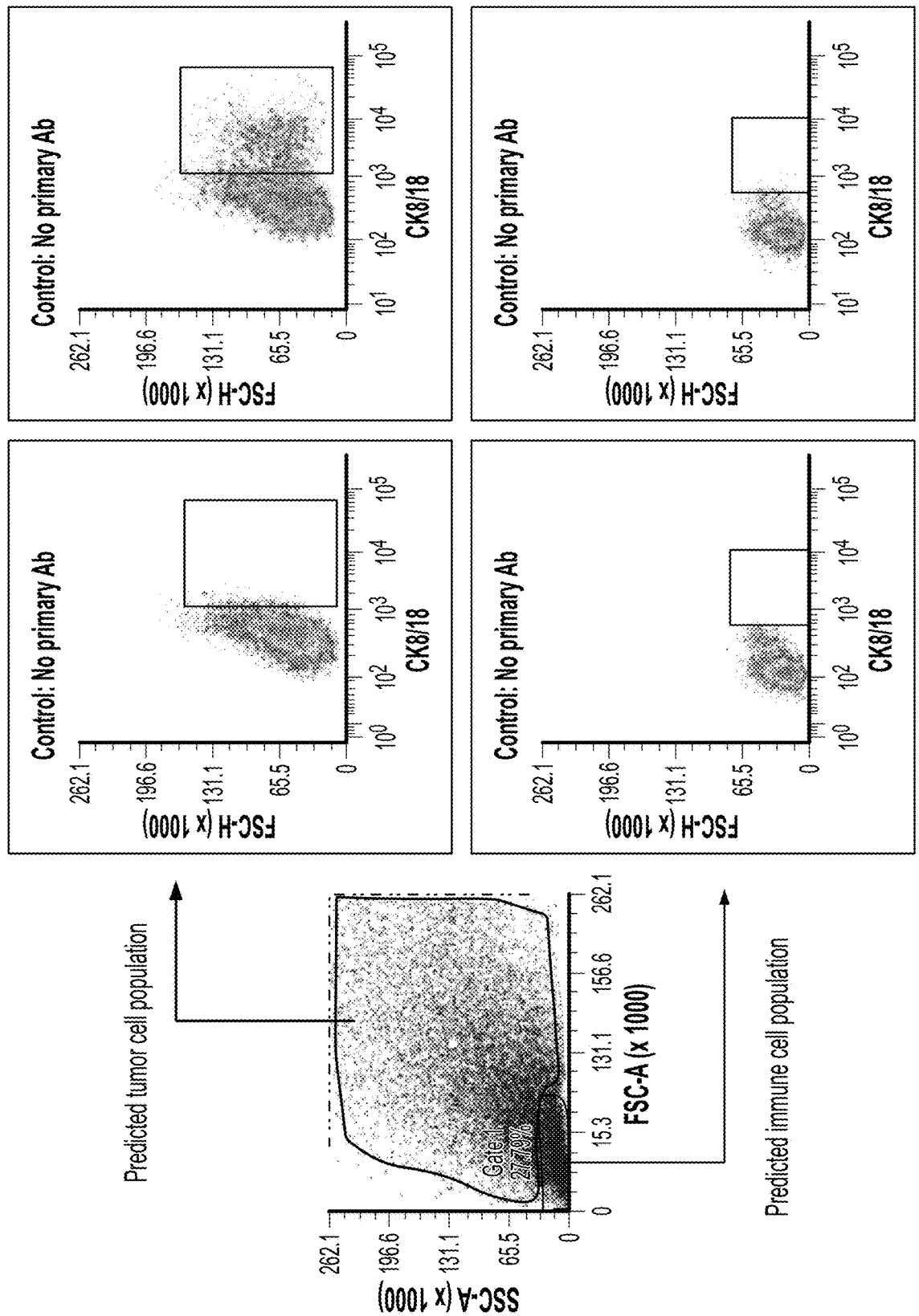
FIG. 8B illustrates the analysis of gated large cells for the CD3 marker (top two panels). The upper right panel shows the control, where no primary antibody was added and the upper left panel shows the actual sample. The rectangle in each panel shows where the positive cells (CD3 positive cells) should be located. Large cells did not show any CD3 positivity, which was expected since the large cells are mostly tumor cells which do not express the CD3 marker. The bottom panels show the analysis of the small cells for the same CD3 marker. Most of the small cells did express CD3, which was expected since the small cells were immune cells.

To confirm that the primary gating in the above example properly predicted a population of immune cells (i.e. digitally separated immune cells from tumor cells in a homogenized sample), a plot of FSC versus biomarker staining intensity for two different cell populations derived from the same sample (large cell and small cell population) for the same marker (CD3) was made. FIG. 8A provides density plots of FSC versus CD3 biomarker staining illustrating the presence of cells in a predicted immune cell population returned after primary gating. Control samples are comparatively illustrated for each population where there is no staining with an antibody targeting CD3. Likewise, FIG. 8B provides density plots of FSC versus CK8/18 tumor biomarker staining illustrating the presence of cells in a predicted tumor cell population returned after primary gating. Again, control samples are comparatively illustrated for each population where there is no staining with an antibody targeting the CK8/18 tumor biomarker. By comparing FIGS. 8A and 8B, it is evident that the gating strategy properly predicted the immune cell population based on the size of the cells.

Figure 7:
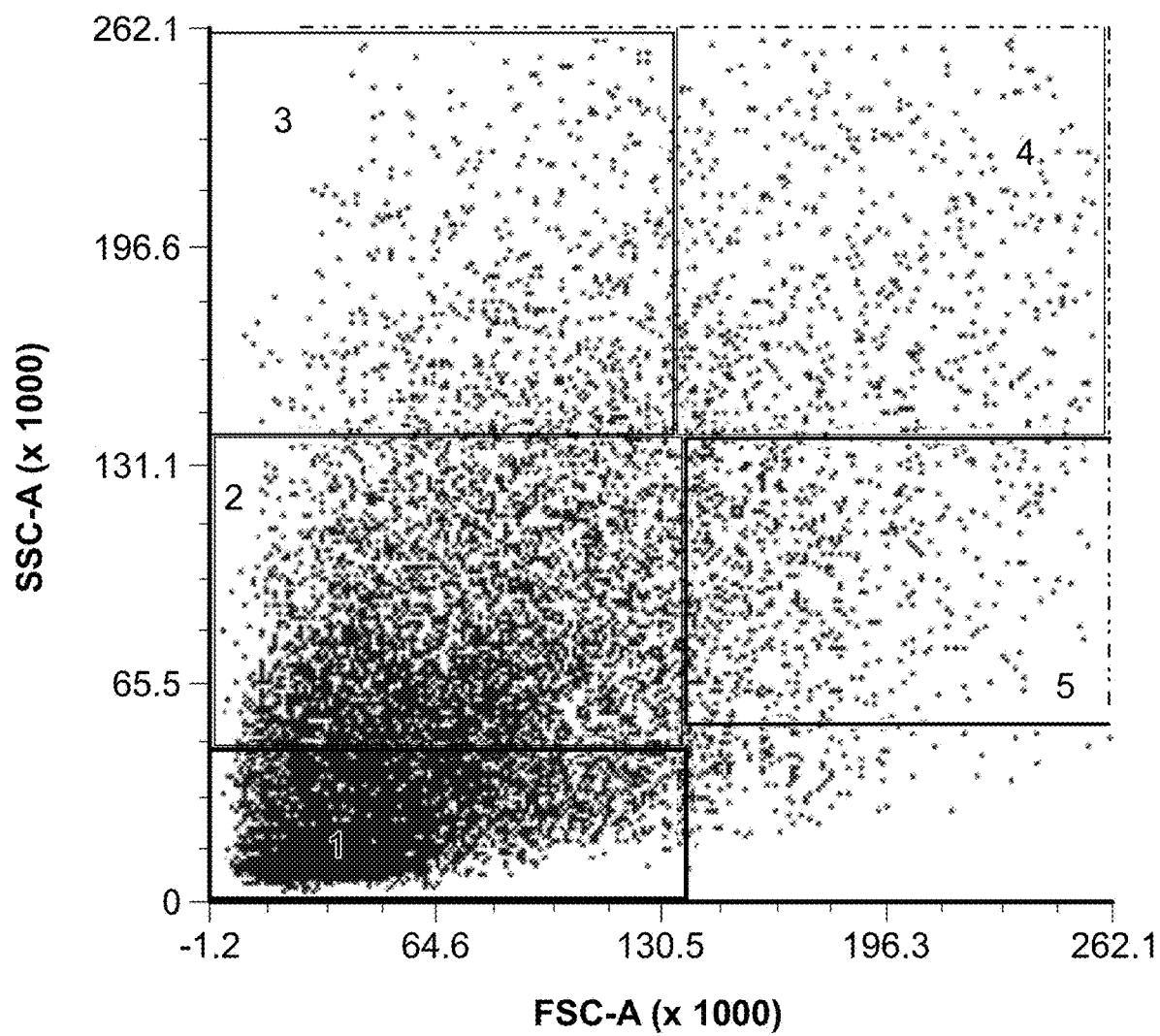
FIG. 7 illustrates a density plot (FSC versus SSC) of a filtered homogenate, where five gatings are selected based on scattering.

The utility of primary gating in predicting cell populations derived from a heterogeneous, homogenized tumor sample based on size and/or granularity is further exemplified in FIG. 7 which illustrates five different gate traces (labeled 1, 2, 3, 4, and 5) performed on a single homogenized sample. Each gate trace, i.e. traces 1, 2, 3, 4, and 5, was selected to provide a different population of cells having different properties based on scattering. In this particular example, gates were selected based on those likely to have aneuploidy, i.e. the presence of an abnormal number of chromosomes. Knowing that such abnormal cells are likely tumor cells and therefore large, gates 4 and 5 were traced to obtain populations enriched which large cells. 13.22% and 8.89% of the cells in the subpopulations generated with gate traces 4 and 5 had aneuploidy, as compared with gate trace 1 (predicted to have small cells, such as immune cells) where only 0.64% of the cells had aneuploidy. 2.14% and 2.32% of the cells in traces 2 and 3, respectively, had aneuploidy based on a trace selection predicted to encompass those cells having higher granularity as compared with the trace selected for gate 1. Here, the optimum gate for capturing a subpopulation having the most cells with aneuploidy was gate 4, which took into consideration high granularity and large cell size, both of which were believed to be characteristic of cells having aneuploidy. Applicant has shown that a primary gating based on forward and side scattering provides a better estimation of aneuploidy than primary gating based on the presence of a tumor marker (e.g. CK8/18) as set forth in Example 3.

Figure 9A:
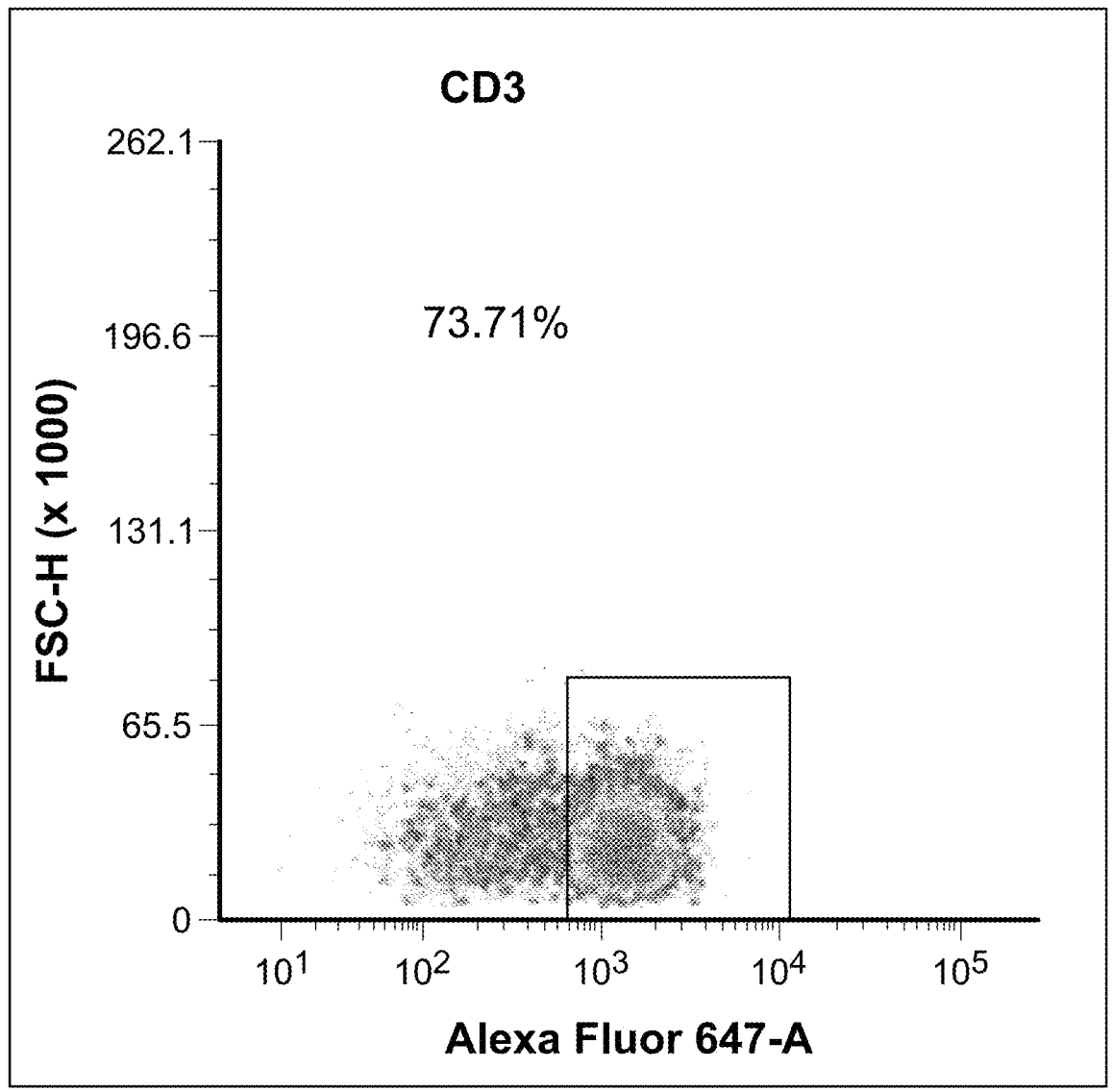
FIG. 9A illustrates a density plot (FSC versus CD3 staining intensity) for a first sub-population expressing the CD3 biomarker.
Figure 9B:
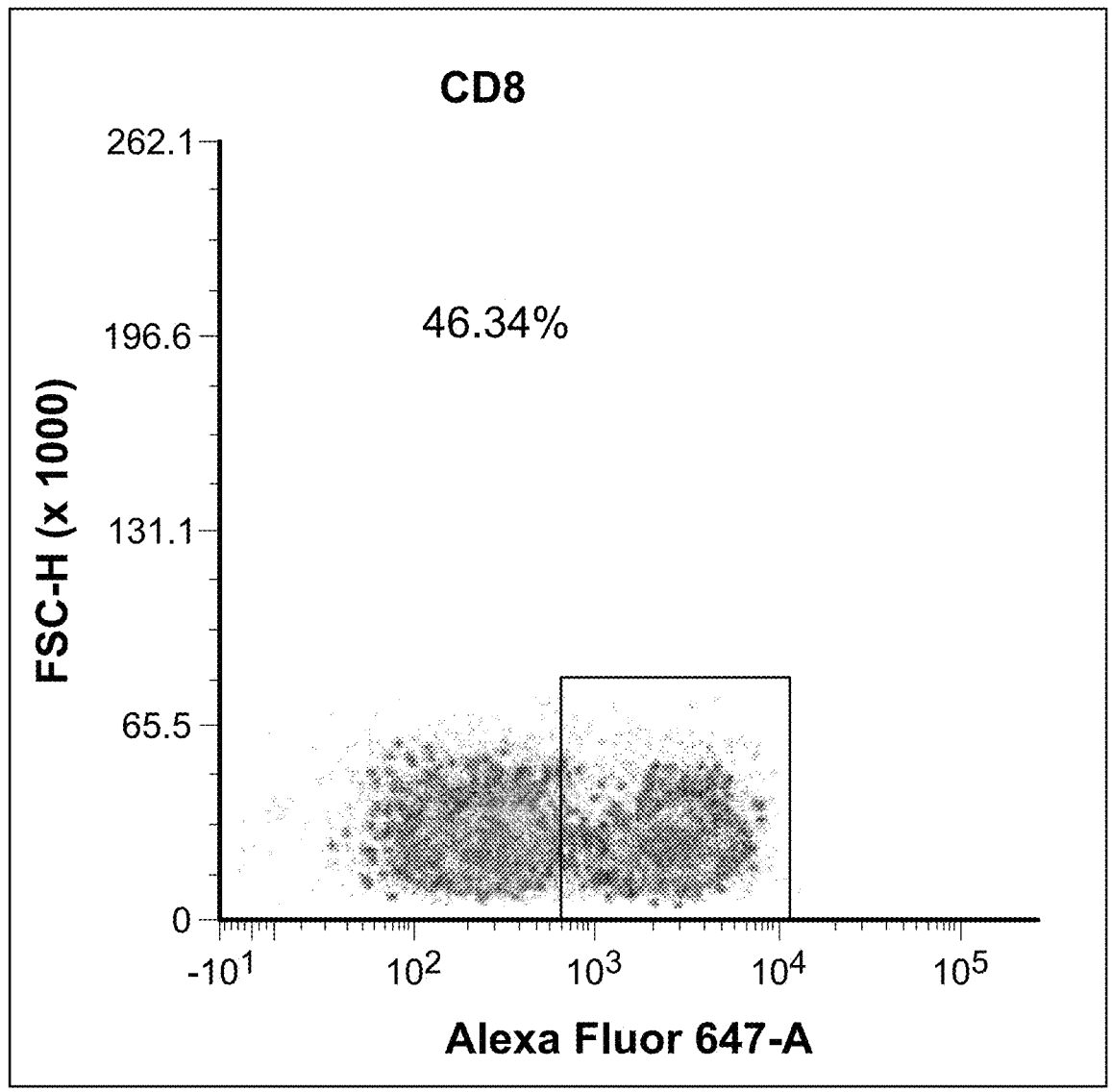
FIG. 9B illustrates a density plot (FSC versus CD8 staining intensity) for a first sub-population expressing the CD8 biomarker.
Figure 9C:
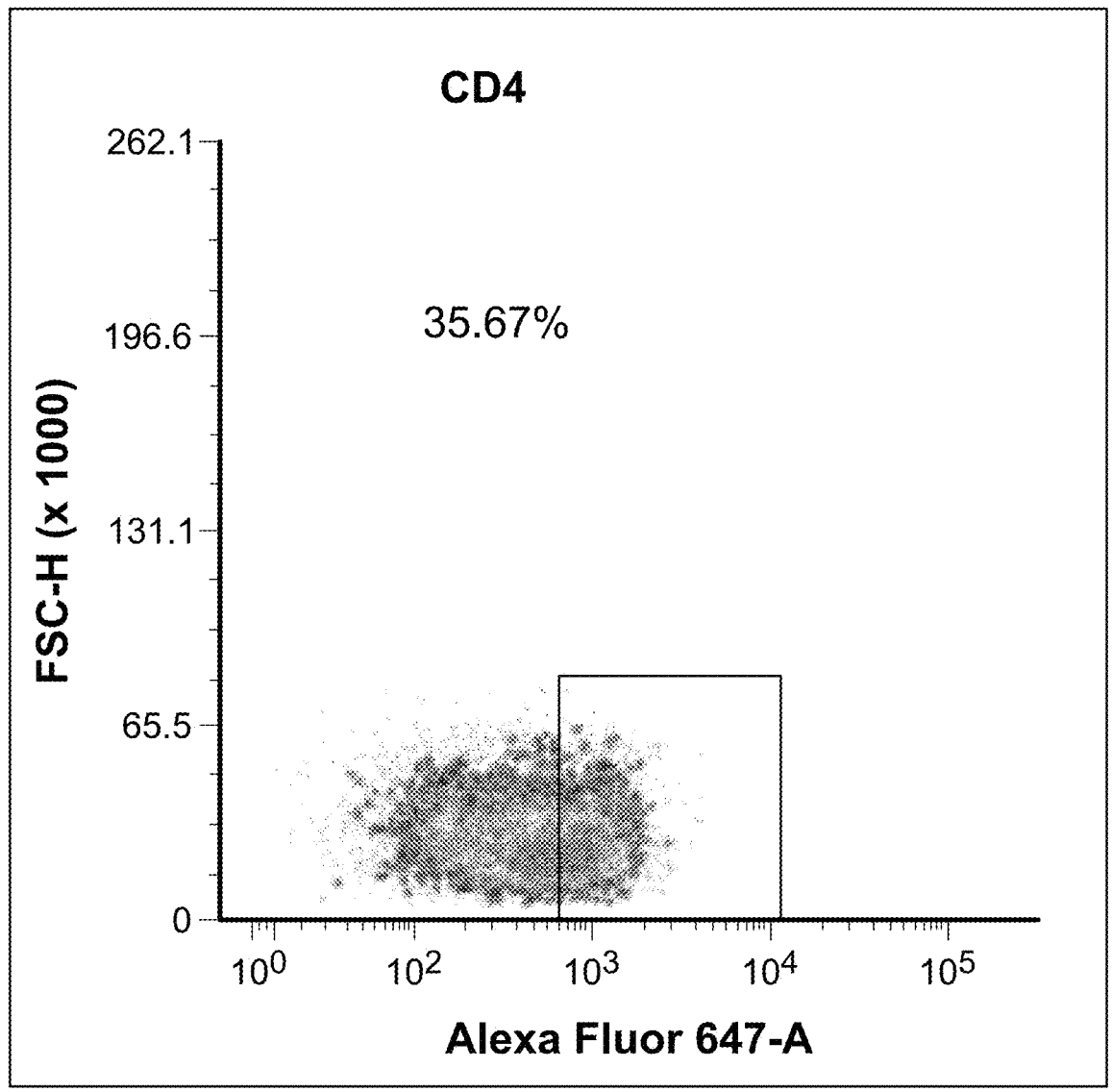
FIG. 9C illustrates a density plot (FSC versus CD4 staining intensity) for a first sub-population expressing the CD4 biomarker.
Figure 10:
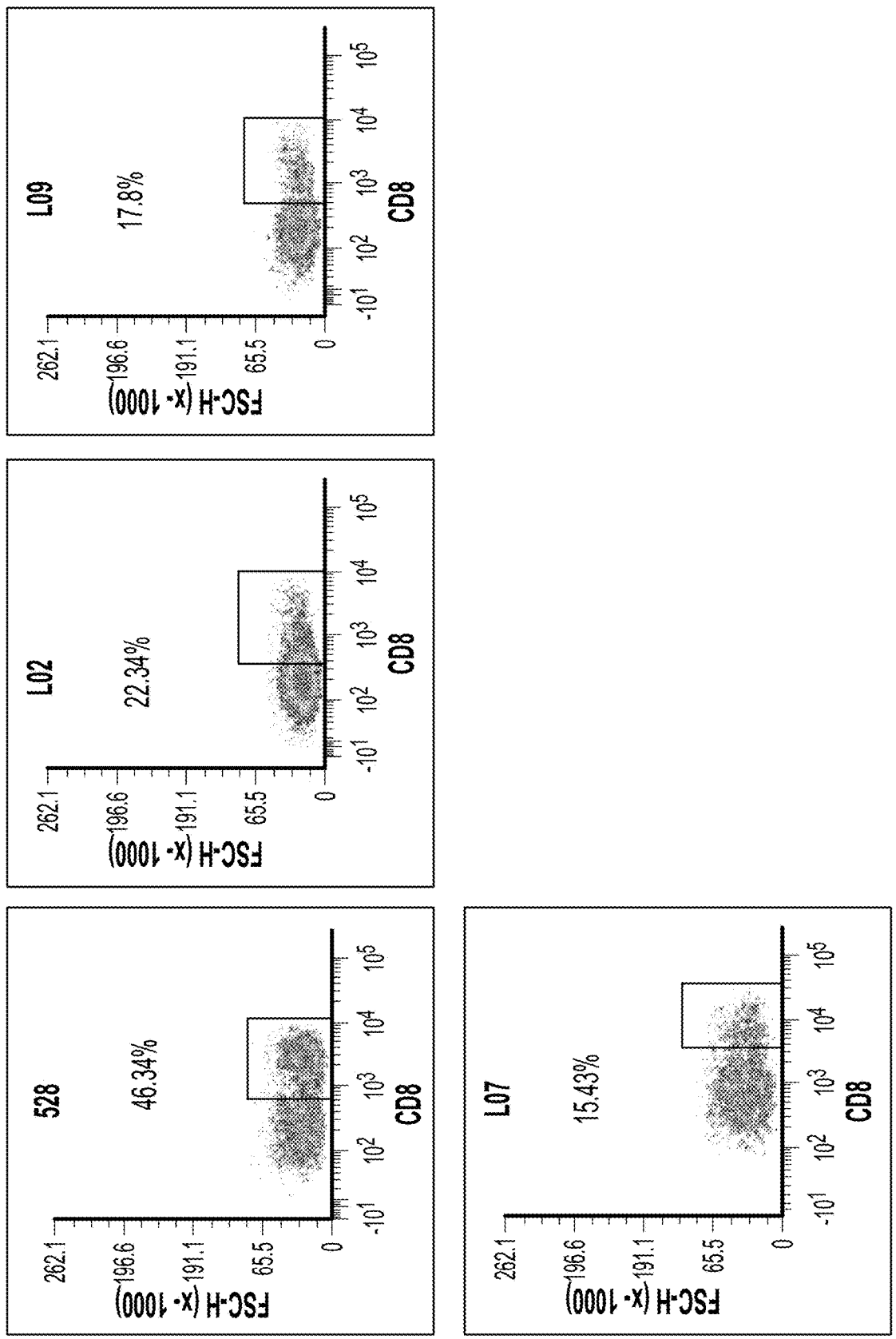
FIG. 10 illustrates density plots (FSC versus CD8 staining intensity) for a sub-population of cells derived from different homogenized lung tumor samples.

In some embodiments, a secondary gating (step 210 or step 240) is performed to determine the expression patterns of particular cell types from within the population of cells identified during primary gating. It is believed that this is particularly useful as the number of biomarkers increases. For example, sequential secondary gatings (step 350, as indicated by the dashed line) may be used in a multiplex assay to identify specific cell sub-populations expressing different biomarkers in the homogenized sample. In some embodiments, each secondary gating is performed by applying a trace to a two-parameter density plot of forward scatter (FSC) versus biomarker staining intensity on the first population of cells identified after a primary gating step By way of example, lymphocytes may be identified by performing a primary gating based on forward and side scattering (see FIG. 6). A first secondary gating may be performed to identify and quantify the CD3 positive T cells (FIG. 9A). Second and third secondary gatings may likewise be performed to differentiate the CD3 positive T cells, based on the expression of CD4 and CD8 (see FIGS. 9B to 9C). In this particular example, three secondary gatings are performed and a trace, having a particular intensity cutoff, is applied to identify those sub-populations expressing each of the CD3, CD8, and CD4 biomarkers. The percentages of biomarker expression for each sub-population may also be determined following secondary gating. FIG. 10 illustrates the generation of the percentages of CD8 positive immune cells derived from homogenized samples from different patient samples. In some embodiments, this type of data can be used to quantitatively measure the expression of different markers from a whole tumor samples dissociated into single cells. In some embodiments, these level of expressions could be correlated to diagnostic, prognostic and therapeutic status of a patient. In some embodiments, flow cytometry, as compared with IHC, is more quantitative and amenable for multiplexing. In some embodiments, the fact that a whole tumor is analyzed may account for increased tumor heterogeneity and may provide better correlations. Applicant has shown that such data acquired by means of the present methods compares well with data acquired from actual physical sorting methods, such as set forth in Example 1.

In some embodiments, the same or different gate for each marker is selected depending on the variability between flow cytometry runs. Gates are then selected which help identify positive cells (cells that did not exist in a control and only appear in a sample). In some processes, the process is automated using a computer-implemented algorithm.

The above principles may be extended to other biomarkers to identify and/or quantify other types of immune cells, and or to identify yet further sub-populations within any population or sub-population. For example, the relative expression of CD28 and CD45RA biomarkers may be used to identify CD45RA+CD28+ naïve cells, CD45RA−CD28+ memory cells and CD45RA+CD28− effector cells, such as based on CD4 and CD8 populations. This principle can be continued with yet additional markers.

The above-identified methods are not limited to quantifying amounts or relative amounts of cells expressing cluster of differentiation markers. In some embodiments, the method described above can be applied to determine a percentage of a type of immune cell in different patients and to determine, for example (i) whether those patients would benefit, for example, from a particular type of therapy; or (ii) to monitor tumor progression and/or treatment. In other embodiments, the methods of the present disclosure may be utilized to identify new correlations between the expression of two or more biomarkers or the expression of a biomarker and a chromosomal abnormality as set forth in Example 2.

EXAMPLES

Example 1—Comparison of Physical Sorting Versus Digital Sorting

Figure 11A:
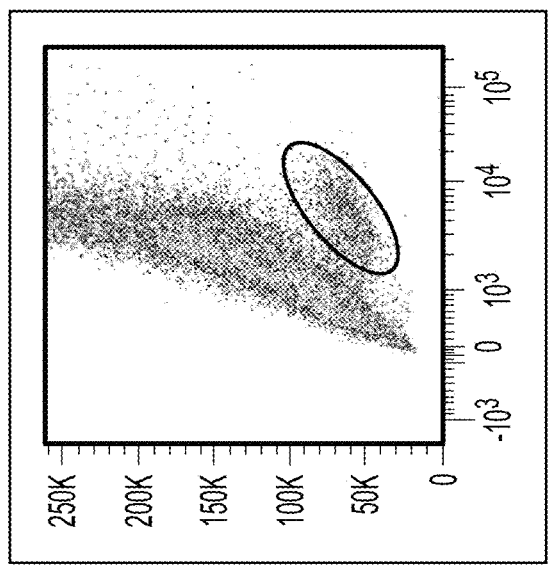
FIGS. 11A-C compare unsorted cells from a homogenized tumor sample (FIG. 11C) as compared with CD3 expression after physical sorting (FIG. 11A) and CD3 expression after digital sorting (FIG. 11B), where both physical sorting and digital sorting improve upon the quality of data and allow for the derivation of accurate percentile values.
Figure 11B:
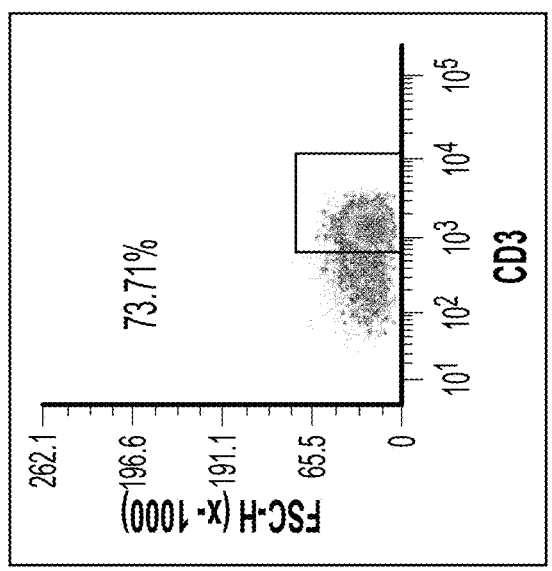
Figure 11C:
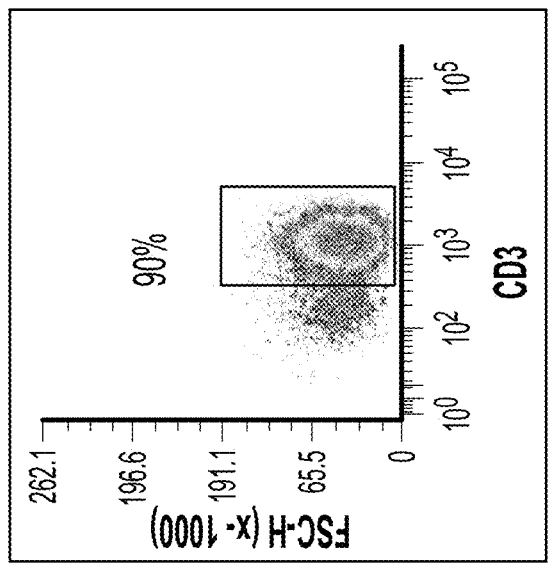

The results from a physical sorting process has been compared with those from a digital gating method according to the methods set forth herein. Physically sorted small cells were analyzed for the CD3 marker (small cells from whole homogenate). Small cells (immune cells) expressed the CD3 marker as expected (see FIG. 11A, which shows the separate and distinct CD3 population (73.71% positive cells)). Overall, FIG. 11 shows that physical and digital sorting methods provide similar results. All cells from a dissociated tumor were stained for CD3 and DAPI, analyzed by flow cytometry, small cells (immune) were gated are presented in FIG. 11A. Gating is a way to look at one population (here, immune cells) within a mixed cell population. All cells from a dissociated tumor were stained for DAPI only and then analyzed by flow cytometry. Small cells (immune cells) were sorted (physically separated from the cell mixture), stained for CD3, and then analyzed again by flow cytometry. The data is presented in FIG. 11A. The percentage in both cases represent the percentage of positive cells within the analyzed population. In case of FIG. 11A, the analyzed population are sorted cells (pure sample) so the percentage was quite high. In the case of FIG. 11B, the analyzed sample was gated into a small cells population which is less pure (some larger cells may find their way in that analyzed population), so the percentage was lower. FIG. 11C, illustrates the analysis on the same cell mixture without gating or sorting. The data was much worse in quality (smearing, lower percentage, non-distinct positive cell populations).

Example 2—Correlation Between Cells Identified as CD8+ and Aneuploidy

Figure 13:
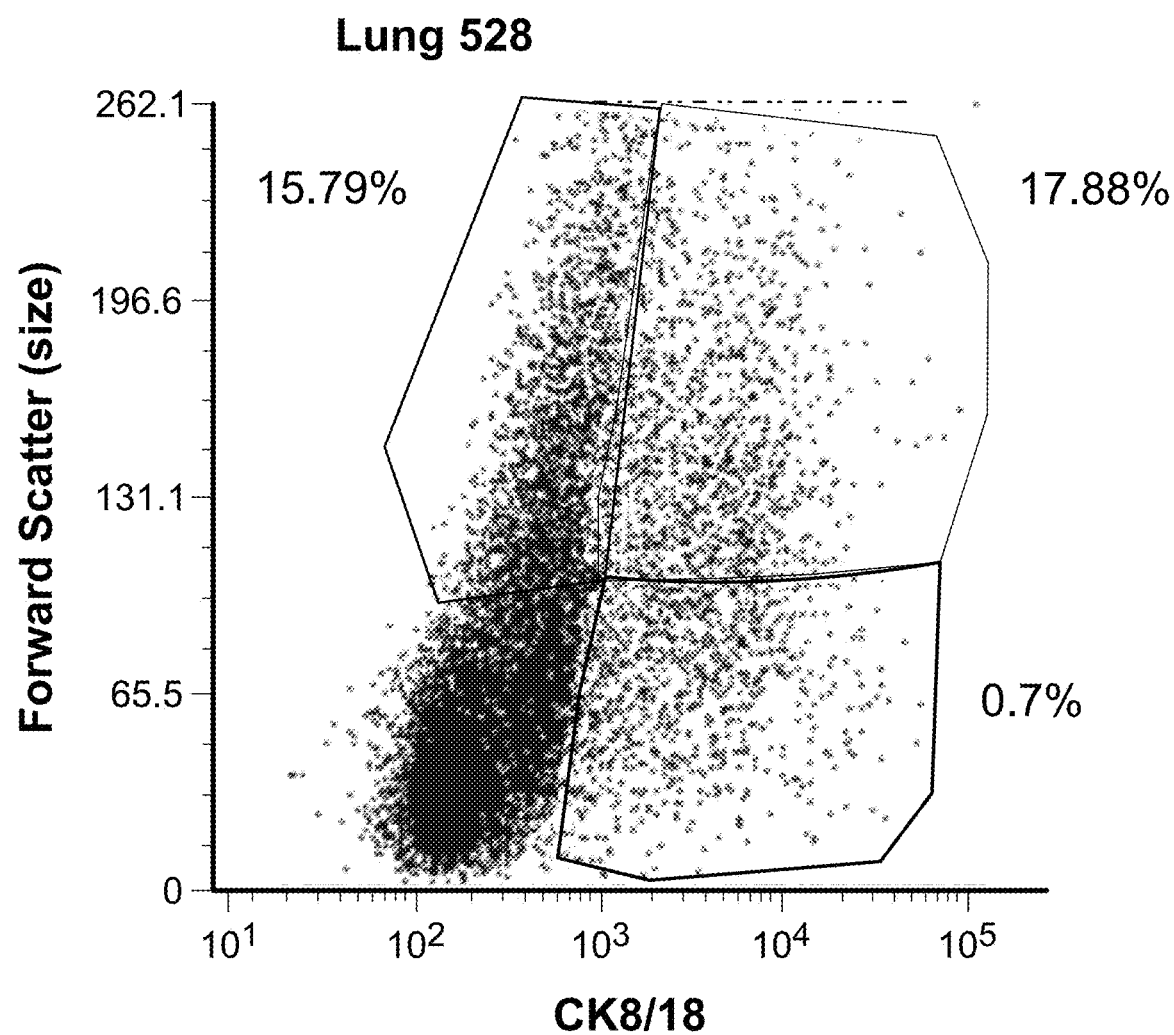
FIG. 13 illustrates a density plot of CK8/18 versus forward scatter.

It is believed that tumor aneuploidy and tumor infiltrating lymphocytes are inversely proportional in different cancer types. We used a tumor homogenate and flow cytometry to analyze a sample for both aneuploidy and tumor infiltrating lymphocytes, and the same correlation was observed. For example, a whole tumor same was homogenized and filtered according to the techniques described herein. An aliquot of the dissociated cells were then stained for the presence of CD3 or CD3, and also stained with DAPI (2-(4-Amidinophenyl)-1H-indole-6-carboxamidine). The stained sample provide for flow cytometry analysis and the data generated was analyzed for aneuploidy (from DAPI) and the marker (CD3 or CD8). The sample process was repeated for different cancer types, e.g. lung cancer and colon cancer. Once again, it was observed that tumor aneuploidy and tumor infiltrating lymphocytes are inversely proportional in different cancer types Example 3—Comparison Between Primary Gating Based on Scattering Versus Primary Gating Based on Biomarker Expression FIG. 7 provides a dot plot showing forward and side size (size versus granularity). When different locations on the plot were analyzed, it was observed that aneuploidy increased with size and with granularity, which was expected since tumor cells are comparatively larger and more granular than aneuploid cells. The same analysis was also performed but using a dot plot showing CK8/18 staining versus forward scatter (FIG. 13). Larger cells were determined to be more aneuploid as expected and CK8/18 were also expected to be more aneuploid. It was also determined that size was an even better predictor of tumor cells than CK8/18 because small cells, which are believed to be CK8/18 positive (bottom right quadrant of FIG. 13) had almost no aneuploidy, meaning that they were most likely non-tumor cells. All large cells (CK8/18 positive or negative) had a much higher aneuploidy, meaning that they were tumor cells. Both FIGS. 7 and 13 confirm that proper gating on size was sufficient to define cells as tumor or immune without the need for staining for a tumor biomarker.

ADDITIONAL EMBODIMENTS

Additional Embodiments 1. A method of quantifying a percentage of cells expressing one or more biomarkers comprising:
  homogenizing a whole tumor sample to provide a homogenized sample;
  staining the cells in the homogenized sample for the presence of the one or more biomarkers;
  performing at least a first primary gating of the cells in the homogenized sample based on size and granularity scattering to provide at least a first population of cells having a first predicted cell type; and
  determining a first percentage of cells expressing a first of the one or more biomarkers in a first sub-population within the first population of cells.

Additional Embodiments 2. The method of additional embodiment 1, wherein the method does not require a physical sorting step prior to determining the first percentage of cells in the at least first sub-population of cells.

Additional Embodiments 3. The method of additional embodiment 1 or 2, wherein the first predicted cell type are immune cells.

Additional Embodiments 4. The method of additional embodiment 3, wherein the immune cells have a size of less than about 12 μm.

Additional Embodiments 5. The method of additional embodiment 3, wherein the first percentage of cells in the first sub-population expressing the first of the one or more biomarkers is determined by performing a secondary gating of the cells in the first population based on the presence of the first of the one or more biomarkers.

Additional Embodiments 6. The method of additional embodiment 5, wherein the first of the one or more biomarkers is selected from the group consisting of a CD3, CD4, CD8, CD45RA, and CD45RO cluster of differentiation biomarker.

Additional Embodiments 7. The method of additional embodiment 6, further comprising determining a second percentage of cells in a second sub-population within the first population of cells expressing a second of the one or more biomarkers, wherein the first and second of the one or more biomarkers are different.

Additional Embodiments 8. The method of additional embodiment 7, wherein the second of the one or more biomarkers is a cluster of differentiation marker.

Additional Embodiments 9. The method of additional embodiment 7, wherein the second of the one or more biomarkers is selected from the group consisting of PD-1, TIM-3, LAG-3, CD28, CD57, and FOXP3.

Additional Embodiments 10. The method of additional embodiment 7, wherein the first of the one or more biomarkers is CD3, and wherein the second of the one or more biomarkers is a biomarker which differentiates the immune cells as regulatory, helper, or cytotoxic T cells.

Additional Embodiments 11. The method of additional embodiment 6, further comprising performing a second primary gating of the cells in the homogenized sample to provide at least a second population of cells having a second predicted cell type.

Additional Embodiments 12. The method of additional embodiment 11, wherein the second predicted cell type are tumor cells.

Additional Embodiments 13. The method of additional embodiment 12, further comprising determining a third percentage of cells within the second population of cells having a chromosomal abnormality.

Additional Embodiments 14. The method of additional embodiment 13, further comprising correlating the determined third percentage of cells having the chromosomal abnormality with the determined first percentage of cells expressing the first of the one or more biomarkers.

Additional Embodiments 15. The method of any of additional embodiments 1 to 14, wherein the homogenized tissue sample is further processed prior to staining, wherein the further processing comprises at least one of digesting proteins within the homogenized sample, heating the sample, or filtering the homogenized sample.

Additional Embodiments 16. The method of additional embodiment 1, further comprising making a treatment decision based partially on the determined percentage of cells in the first sub-population expressing the first of the one or more biomarkers.

Additional Embodiments 17. A method of quantifying a percentage of cells expressing at least a first biomarker of a plurality of biomarkers in a tissue sample comprising:
  homogenizing a tissue sample to provide a homogenized sample;
  staining the cells in the homogenized sample for the presence of the plurality of biomarkers;
  performing a primary gating of the cells in the homogenized sample based on scattering to provide at least a first population of cells having a first predicted size range;
  performing at least one secondary gating of the cells in the first population, wherein the at least one secondary gating is based at least on the presence of a first biomarker of the plurality of biomarkers, and wherein the at least one secondary gating provides a first sub-population of cells expressing the first biomarker of the plurality of biomarkers; and
  determining a percentage of cells expressing the first biomarker of the plurality of biomarkers in the first sub-population of cells.

Additional Embodiments 18. The method of additional embodiment 17, wherein the method does not require a physical sorting step prior to determining the percentage of those cells in the first sub-population.

Additional Embodiments 19. The method of additional embodiment 17 or 18, wherein the first population of cells have a first predicted size of less than about 12 μm.

Additional Embodiments 20. The method of any of additional embodiments 17 to 19, wherein the homogenized sample is stained for at least the presence of a CD3 biomarker. Additional Embodiments 21. The method of additional embodiment 20, wherein the homogenized sample is further stained for the presence of at least one additional cluster of differentiation biomarker.

Additional Embodiments 22. The method of additional embodiment 20, wherein the at least one secondary gating is based on at least the presence of the CD3 biomarker.

Additional Embodiments 23. The method of additional embodiment 21, wherein separate secondary gatings are independently performed based on the presence of the CD3 biomarker and at least one of a CD4 biomarker and a CD8 biomarker, to provide a CD3 sub-population, and at least one of a CD4 sub-population and a CD8 sub-population.

Additional Embodiments 24. The method of additional embodiment 23, wherein the percentage of cells in the CD3 sub-population and the at least one of the CD4 and CD8 sub-populations are independently determined.

Additional Embodiments 25. The method of any of additional embodiments 17 to 24, wherein the tissue sample is derived from at least one of a whole tumor, a partial tumor, a metastatic tumor, a partial metastatic tumor, or lymph nodes.

Additional Embodiments 26. The method of any of additional embodiments 17 to 24, wherein the tissue sample is derived from at least one of residual surgical material or a biopsy sample.

Additional Embodiments 27. The method of any of additional embodiments 17 to 26, wherein the homogenized tissue sample is further processed prior to staining, wherein the further processing comprises at least one of digesting proteins within the homogenized sample, heating the sample, or filtering the homogenized sample.

Additional Embodiments 28. The method of any of additional embodiments 17 to 27, wherein the plurality of biomarkers are selected from the group consisting of cluster of differentiation biomarkers, PD-1, TIM-3, LAG-3, and FOXP3.

Additional Embodiments 29. The method of additional embodiment 28, wherein the cluster of differentiation biomarkers are selected from the group consisting of CD3, CD4, CD8, CD45RA, CD45RO, CD28, and CD57.

Additional Embodiments 30. A method of quantifying a percentage of cells expressing at least a first of one or more biomarkers in a homogenized tissue sample comprising:
 filtering the homogenized tissue sample to provide a filtered homogenized sample;
 staining the cells in the filtered homogenized sample for the presence of the one or more biomarkers;
 performing at least two sequential gatings to provide at least a first sub-population of cells expressing the first of the one or more biomarkers; and
 determining a first percentage of cells expressing the first of the one or more biomarkers in the first sub-population.

Additional Embodiments 31. The method of additional embodiment 30, wherein the at least two sequential gatings comprise a primary gating to provide a first population of cells and a secondary gating to provide the first sub-population of cells.

Additional Embodiments 32. The method of additional embodiment 31, wherein the primary gating is based on forward scattering and side scattering.

Additional Embodiments 33. The method of additional embodiment 32, wherein a cutoff is selected for forward scattering such that the first population is enriched with immune cells.

Additional Embodiments 34. The method of additional embodiment 33, wherein a plurality of secondary gatings are conducted.

Additional Embodiments 35. The method of additional embodiment 34, wherein secondary gatings are performed for at least two cluster of differentiation biomarkers.

Additional Embodiments 36. The method of additional embodiment 35, wherein the cluster of differentiation biomarkers are selected from the group consisting of CD3, CD4, CD8, CD45RA, CD45RO, CD28, and CD57.

Additional Embodiments 37. The method of any of additional embodiments 31 to 36, further comprising determining a second percentage of cells in a second sub-population of cells expressing a second of the one or more biomarkers, wherein the first and second of the one or more biomarkers are different.

Additional Embodiments 38. The method of additional embodiment 37, wherein the second of the one or more biomarkers is a biomarker other than a cluster of differentiation marker.

Additional Embodiments 39. The method of additional embodiment 38, wherein the second of the one or more biomarkers is selected from the group consisting of PD-1, TIM-3, LAG-3, and FOXP3.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

The invention claimed is:

1. A method of quantifying a percentage of cells expressing one or more biomarkers comprising:
 obtaining a fixed surgical sample derived from a fixed residual surgical sample, a fixed biopsy sample, or a fixed histological sample;
 mechanically shearing the obtained fixed surgical sample to provide a homogenized sample, wherein any heterogeneity of cells within the obtained fixed surgical sample is substantially uniformly distributed within the homogenized sample such that any aliquot removed from the homogenized sample expresses the heterogeneity of the fixed surgical sample;
 staining the cells in the homogenized sample for the presence of the one or more biomarkers;
 obtaining flow cytometry data based on the stained cells in the homogenized sample;
 performing a first primary gating of the stained cells in the obtained flow cytometry data based on size and granularity scattering to provide a first population of cells having a first predicted cell type;
 determining a percentage of cells expressing a first of the one or more biomarkers in a first sub-population within the first population of cells;
 performing a second primary gating of the obtained flow cytometry data to provide at least a second population of cells having a second predicted cell type, and wherein the second predicted cell type are tumor cells;
 determining a percentage of cells within the second population of cells having a chromosomal abnormality; and
 correlating the determined percentage of cells having the chromosomal abnormality with the determined percentage of cells expressing the first of the one or more biomarkers.

2. The method of claim 1, wherein the method does not require a physical sorting step prior to determining the percentage of cells expressing the first of the one or more biomarkers in the first sub-population within the first population of cells.

3. The method of claim 1, wherein the first predicted cell type are immune cells, and wherein the immune cells have a size of less than about 12 μm.

4. The method of claim 3, wherein the percentage of cells expressing the first of the one or more biomarkers in the first sub-population within the first population of cells is determined by performing a secondary gating of the cells in the first population based on the presence of the first of the one or more biomarkers.

5. The method of claim 4, wherein the first of the one or more biomarkers is selected from the group consisting of a CD3, CD4, CD8, CD45RA, and CD45RO cluster of differentiation biomarker.

6. The method of claim 5, further comprising determining a percentage of cells expressing a second of the one or more biomarkers in a second sub-population within the first population of cells, wherein the first and second of the one or more biomarkers are different.

7. The method of claim 6, wherein the second of the one or more biomarkers is a cluster of differentiation marker selected from the group consisting of PD-1, TIM-3, LAG-3, CD28, CD57, and FOXP3.

8. The method of claim 6, wherein the first of the one or more biomarkers is CD3, and wherein the second of the one or more biomarkers is a biomarker which differentiates the immune cells as regulatory, helper, or cytotoxic T cells.

* * * * *